United States Patent
Haight et al.

[19]

[11] Patent Number: 6,129,699
[45] Date of Patent: Oct. 10, 2000

[54] PORTABLE PERSISTALTIC PUMP FOR PERITONEAL DIALYSIS

[75] Inventors: Levoy G. Haight, West Jordan; Royce Herbst, Alpine; Reed F. Winterton; James L. Sorenson, both of Salt Lake City, all of Utah

[73] Assignee: Sorenson Development, Inc., Salt Lake City, Utah

[21] Appl. No.: 08/961,757

[22] Filed: Oct. 31, 1997

Related U.S. Application Data

[60] Provisional application No. 60/030,176, Nov. 1, 1997.

[51] Int. Cl.[7] .......................... A61M 1/00; A61M 37/00; F04B 49/06
[52] U.S. Cl. .................... 604/29; 604/5.04; 604/6.11; 604/30; 604/31; 417/477.2; 417/44.2
[58] Field of Search ...................... 604/4–5, 19, 27–34, 604/153, 155; 417/477.2–477.6, 477.9, 477.12–477.13, 44.2

[56] References Cited

U.S. PATENT DOCUMENTS

| | | |
|---|---|---|
| 3,308,825 | 3/1967 | Cruse . |
| 3,620,215 | 11/1971 | Tysk et al. . |
| 3,742,822 | 7/1973 | Talbert . |
| 3,875,941 | 4/1975 | Adair . |
| 3,982,539 | 9/1976 | Muriot . |
| 4,002,170 | 1/1977 | Hansen et al. . |
| 4,068,664 | 1/1978 | Sharp et al. . |
| 4,239,041 | 12/1980 | Popovich et al. . |
| 4,311,587 | 1/1982 | Nose et al. . |
| 4,381,003 | 4/1983 | Buoncristiani . |
| 4,396,382 | 8/1983 | Goldhaber . |
| 4,412,917 | 11/1983 | Ahjopalo . |
| 4,488,961 | 12/1984 | Spencer . |
| 4,498,900 | 2/1985 | Buoncristiani . |
| 4,738,595 | 4/1988 | Gaiser . |
| 4,820,265 | 4/1989 | DeSatnick et al. ................ 604/30 |
| 5,029,580 | 7/1991 | Radford et al. . |
| 5,141,493 | 8/1992 | Jacobsen et al. ................ 604/29 |
| 5,195,960 | 3/1993 | Hossain et al. ................ 604/34 |
| 5,282,787 | 2/1994 | Wortrich ................ 604/30 |
| 5,336,173 | 8/1994 | Folden ................ 604/29 |
| 5,338,293 | 8/1994 | Jeppsson et al. ................ 604/29 |
| 5,397,222 | 3/1995 | Moss et al. . |
| 5,438,510 | 8/1995 | Bryant et al. ................ 364/413.11 |
| 5,445,506 | 8/1995 | Afflerbaugh et al. . |
| 5,480,294 | 1/1996 | Di Perna et al. . |
| 5,518,378 | 5/1996 | Neftel et al. . |
| 5,556,263 | 9/1996 | Jacobsen et al. . |
| 5,626,563 | 5/1997 | Dodge et al. ................ 604/153 |
| 5,628,908 | 5/1997 | Kamen et al. . |
| 5,632,606 | 5/1997 | Jacobsen et al. . |
| 5,643,201 | 7/1997 | Peabody et al. . |
| 5,655,897 | 8/1997 | Neftel et al. . |
| 5,713,850 | 2/1998 | Heilmann et al. ................ 604/28 |

OTHER PUBLICATIONS

International Search Report, mailed Feb. 18, 1999 (3 pages).

*Primary Examiner*—Mark O. Polutta
*Assistant Examiner*—Patricia M. Bianco
*Attorney, Agent, or Firm*—Trask Britt

[57] ABSTRACT

A pump assembly for ambulatory peritoneal dialysis transfer procedures includes a portable power supply geared to drive a high-volume peristaltic pump. A cassette of the pump comprises an encasement; tubing including an inner portion positioned within the encasement, a patient-side portion for connection to an indwelling peritoneal dialysis catheter and an opposing portion connectable to a system for containment and communication of a peritoneal dialysis solution which may be one single-compartment bag assembly; a safety valve for selectively occluding and permitting the communication of the solution through the inner portion; and a filter preferably interposed along the patient-side portion which filters air and particles from peritoneal dialysate that is flowing toward a patient and which allows peritoneal dialysate to flow substantially freely and unfiltered away from the patient.

19 Claims, 20 Drawing Sheets

PORTABLE PERSISTALTIC PUMP FOR PERITONEAL DIALYSIS

CLAIM OF PRIORITY

Pursuant to the provisions of 35 U.S.C. 119(e), this application claims the benefit of the filing date of provisional patent application Serial No. 60/030,176, filed Nov. 1, 1997, for "APPARATUS AND METHOD FOR MICRO-EVACUATION OF SECRETIONS."

BACKGROUND OF THE INVENTION

1. Field

This invention relates to means for evacuating undesired bodily secretions of medical patients. It is more particularly directed to medical pumps, notably peristaltic pumps in filtered conduit systems. It is specifically directed to improved procedures for the fluid transfer stage of kidney dialysis treatments.

2. State of the Art

The medical environment has numerous applications for fluid delivery and suction. During surgery, for example, entry sites must have blood or other fluids evacuated. Emergency care personnel must clean a wound properly during care and cleanup. For example, after-surgery complications can cause the endocrine system to overproduce, building pockets of fluid in and around the lungs, or within the peritoneal cavity. In each case, the excess fluid must be removed. This procedure must be accomplished in a mild, gentle manner to avoid tissue trauma or damage to the surrounding area.

Many fluid delivery systems, particularly in a hospital, outpatient, laboratory or home care environment, utilize pumps. Various types of such pumps are constructed with piston, diaphragm, or peristaltic mechanisms. Some such pumps are capable of bi-directional function. While the majority of medical pumps are relied upon for the infusion of fluids, some are applied to evacuation procedures.

Applications of various liquid handling and delivery systems include infusion of blood and blood products such as in hemodialysis; total perenteral nutrition; chemotherapy; hydration maintenance; transfer of samples from one container to another; and administration of medicaments to tissues, organs, the vascular system or other bodily sites. Other applications include pleural therapy, evacuation of wound weepage and other undesirable bodily secretions as well as transfer of peritoneal dialysate solutions. Such infusion and evacuation procedures typically utilize lower volume pumps.

Though some pumps for micro-volume applications are inexpensive enough to be disposable, as illustrated by U.S. Pat. Nos. 5,556,263 and 5,632,606 to Jacobsen et al., virtually all medical pumps, particularly those of higher-volume systems, notably, those used for peritoneal dialysis, are prohibitively expensive for patient acquisition.

The negative pressure necessary to evacuate fluids is typically generated by means of gravity, a bellows-type container, a resilient bladder or a mechanical pump. Representative such means devices disclosed by U.S. Pat. Nos. 3,875,941 to Adair; 3,982,539 to Muriot; and 3,742,822 to Talbert. The device disclosed in U.S. Pat. No. 5,029,580 to Radford et al. incorporates a multi-lumen endotracheal catheter for simultaneous introduction of therapeutic gases under positive pressure and aspiration of undesirable respiratory secretions and gases under negative pressure. Additional lumens may be incorporated for introduction of medication and lavage solutions. Provision may also be made for monitoring pressures, temperatures and catheter tube flow rates. The interaction of negative and positive pressures at the distal (patient) tip of such catheters combined with tip perforations and curvatures results in homogenization of localized secretions and gases, resulting in more efficient aspiration.

Screening at the distal tip of such devices may be accomplished by structure such as those disclosed in U.S. Pat. Nos. 3,308,825 to Cruse; 4,002,170 to Hansen et al.; and 4,068,664 to Sharp et al.

Existing evacuation devices suffer from various disadvantages. Flow rates tend to be either fixed or irregular, and are insufficiently regulated. Flows are typically uni-directional. Costs are prohibitively high for disposability, adversely impacting the ambulatory user. Operation is excessively complicated, unduly limiting the home care user.

There is a need for a low-volume, micro-evacuator device, wherein electronic circuitry enables regulated flow rates in alternate directions of flow in a selected, even adjustable, net-suctioning pattern. This mode of operation would prevent obstruction of the suction catheter and enhance the reliability of secretion flow. There is also a need for an inexpensive high-volume medical pump.

It would also be advantageous for a micro-evacuator device to be constructed (1) unobtrusively to enable ongoing suction of undesired bodily fluids throughout ambulation of a patient; (2) sufficiently inexpensive to be disposable; (3) sufficiently simple for use in a home care environment and/or (4) with a real-time monitor and indicator of catheter pressure and other important variables.

In low-volume applications it is necessary or desirable to provide pump portability to reduce health care costs and enhance patient comfort, convenience, ambulatory productivity and overall lifestyle. For identical reasons it would be desirable to achieve portability for high-volume pumping applications, such as peritoneal dialysis. Current high-volume pumps incorporate bulky, heavy and expensive features such as AC powered liquid warming chambers, alarms for obstruction, volumetric and pressure monitoring, programmable actuation schedules and bidirectional flow. Accordingly, they are generally stationary, and not portable. U.S. Pat. Nos. 4,381,003 and 4,498,900 to Buoncristiani and 5,438,510 to Bryant et al. disclose such elements. There remains a need for a small, light-weight and portable medical pump to support high-volume transfers.

During a typical peritoneal dialysis procedure involving a pump, known as continuous cyclical peritoneal dialysis or CCPD, the pump remains affixed to a power source, and the patient remains attached to the pump for several cycles of infusion and evacuation of dialysate solution throughout the night. The gravity feed/drain approach, known as continuous ambulatory peritoneal dialysis or CAPD, likewise requires patient immobility throughout approximately five such transfers every four to six waking hours involving roughly at least 10 minutes to infuse new dialysate and 20 minutes to drain used dialysate each transfer. There is a need for a medical pump capable of more rapidly transferring high-volumes of dialysate into and out of a patient who may remain ambulatory not only during dialysis but also throughout each transfer procedure.

Presently, both gravity feed and pump methods of performing peritoneal dialysis normally involve drainage of used solution from the peritoneum into an unused receptacle for later disposal. Clean, unused solution is then introduced into the peritoneum from a solution reservoir. These procedures, typical examples of which are illustrated by U.S. Pat. Nos. 3,620,215 to Tysk; 4,396,382 to Goldhaber and 4,412,917 to Ahijopalo, require the use of two separate solution containers. Such procedures presuppose a series of valve or clamp openings and closings in a defined sequence to ensure that solution is directed in accordance with protocol, illustrative of which is FIG. 4 of U.S. Pat. No. 4,239,041 to Popovich et al.

It is important that any pump transfer set provide for facile, clean connection and disconnection of the dialysate containment system to the indwelling catheter tube, whereby to minimize the potential for peritonitis. When an ambulatory patient completes a transfer of dialysis solution through a stationary pump, the patient is normally disconnected from the pump at the indwelling tube. The patient is thereby permitted to move about freely, until being reconnected to continue with the next transfer procedure. Each such exchange exposes a patient to potential contamination. Typical precautions against contamination involve wearing a face mask, closing windows and doors and turning off air conditioning in rooms or vehicles in which exchanges are to take place. These expedients are not entirely effective, and there thus remains a need for an improved arrangement, whereby to minimize this mode of patient exposure.

Though unused dialysis solution is sterile, organic particles and air bubbles are typically carried by the solution. Air bubbles introduced to the patient are known to cause severe muscle pains in the shoulders and chest, until the air diffuses into the surrounding body tissues. Some incidence of non-bacterial peritonitis is known to be associated with the organic materials carried by dialysis solution. An air and particle filter for use in a gravity-feed system is disclosed by U.S. Pat. No. 4,239,041 to Popovich et al. U.S. Pat. No. 4,311,587 to Nose et al. discloses a system in which a filter for use with a pressurized source of fresh dialysate solution is associated with a check valve constructed to permit flow only away from the filter. U.S. Pat. No. 4,488,961 to Spencer discloses a housing for maintaining a filter element in a filtering position during fluid infusion and in a free-flow position during fluid withdrawal. Filters preventing passage of bacteria prevent rapid gravity-flow and are only practical for use with pumps, not gravity flow CAPD. There remains a need for a practical system for screening out air bubbles and filtering particulate matter from fresh dialysate. There is a further need for such a filter to protect against microbial migration to the peritoneal cavity during an exchange of single- or multiple-bag dialysate containment systems.

SUMMARY OF THE INVENTION

The present invention may be envisioned as either improved apparatus or improved procedures enabled by the apparatus. In particular, the invention provides a novel procedure, which may be termed "Ambulatory Transfer Peritoneal Dialysis" (ATPD). This procedure differs from known CAPD and CCPD procedures, in that the patient remains ambulatory during the transfer phase of a dialysis treatment. In general, the procedure is enabled by a special interface between the indwelling tube of the patient and the containers used for waste collection and dialysate supply. This interface couples with a mechanism capable of increasing the head pressure normally inherent in a gravity feed system. This increase in pressure facilitates more rapid exchange, but perhaps more importantly, makes the use of biofilters in the dialysate flow path practical. Volumetric flow rates suitable for peritoneal dialysate Transfer of in excess of 100, typically 300 or more ml/minute through a biofilter capable of excluding bacterial fragments are practical.

Certain preferred embodiments provide for increased head pressure through an inexpensive high-volume, small-sized, light-weight, closed system peristaltic pump assembly. Such an assembly typically comprises a positive displacement pump of the type in which fluid is urged through a resilient, compressible tube by means of traveling compression rollers. Alternative designs incorporate a collapsible dialysate reservoir as a pumping chamber. The flexible plastic bags conventionally used for both fresh and spent dialysate are ideal such reservoirs. A filled such bag may be placed within a mechanism structured (e.g., as a "clam shell") to apply squeezing action, thereby to force dialysate towards a patient at a selected rate and/or pressure. The same mechanism may be adapted to clasp (e.g., by means of adhesive) the walls of a collapsed or partially collapsed reservoir. The mechanism may operate to reconfigure, that is to increase, the internal volume of the container. In this fashion, spent dialysate may be withdrawn by suction, at a selected rate from a patient at the commencement of an exchange.

Some embodiments of the invention utilize an improved version of a positive displacement pump of the type in which a section of elastic tubing functions as a resilient pump chamber. This pump chamber is typically positioned within a housing comprising a support surface for the resilient chamber. Liquid is urged through the chamber by a traveling roller assembly associated with the housing. The roller assembly is structured and arranged to press a roller surface against a section of the resilient chamber towards the support surface, whereby to reduce the transverse cross section of the tubing between the roller surface and the support surface. The roller surface travels away from an inlet to the resilient chamber and towards an outlet from the resilient chamber. The improvement of this invention provides the resilient pump chamber and its support surface in a cassette. The roller assembly is provided in association with a drive mechanism organized such that the roller surface travels repetitively within an open sided housing from an inlet towards an outlet. The open sided housing is structured to receive the cassette in an installed condition. The housing and cassette are mutually adapted so that when the cassette is in its installed condition, the resilient chamber is functionally positioned with respect to the roller assembly. That is, these components are spatially arranged so that the roller surface urges fluid through the chamber. A normally biased-closed valve may be provided in association with the cassette, the valve being structured and arranged to open when the cassette is in its installed condition.

The pumps envisioned by this invention will ordinarily be powered by a small battery, ideally of the rechargeable type. Alternatively, the drive means may comprise a manually operated handle, a detachable power drill or power screwdriver or the like. Such a manual handle, drill or screwdriver may be engaged with a drive train. The drive train may include gear means for reducing the rate of rotation of a driven axle, preferably usable with the power implements; or the drive train may comprise a direct socket in association with the driven axle preferably usable with a manual handle.

A novel transfer set for the exchange of dialysate solution is also provided by this invention. This transfer set includes a length of medical tubing, constituting a bidirectional flow path for dialysate solution between an indwelling patient catheter tube and a dialysate containment system. A first coupling is carried at a first end of this length of medical tubing for connection to an indwelling patient catheter tube. Structure in fluid flow communication with the length of medical tubing constitutes means for directing fresh dialysate solution traveling through the tubing towards the first coupling through a first travel path and directing spent dialysate solution traveling through the tubing from the patient through a second travel path. A biofilter may be positioned in circuit with the first travel path.

In certain preferred embodiments, a check valve assembly in fluid flow communication with the length of medical tubing includes the biofilter and is structured and arranged to filter air and particles from fresh dialysate solution as it flows toward a patient and to allow free, unfiltered flow of spent dialysate solution away from a patient. The transfer may also include a safety valve for selectively permitting flow of a dialysate solution through the length of medical tubing. A segment of this medical tubing may function as the pump chamber of a positive displacement pump of the type described previously in this disclosure.

A high-volume peristaltic pump assembly for portable peritoneal dialysis procedures in accordance with this invention will typically include a portable power supply (typically a rechargeable battery pack). A motor, powered by this power supply generally includes a driven shaft capable of clockwise and counterclockwise rotation. A displacement impeller assembly may be mounted to turn within an impeller chamber in response to rotation of the driven shaft. This impeller assembly typically includes a plurality of roller elements carried through a circular travel path within the impeller chamber. The travel path is situated partially within a zone which presents a receptacle opening into the impeller chamber. A transfer set adapted for use with this assembly will include a cassette configured to install within this receptacle opening to occupy the zone. The cassette constitutes an encasement for a segment of the length of medical tubing, and includes a reaction (tube support) surface constructed and arranged closely to approach the travel path of the roller elements when the cassette is installed within the receptacle opening. The transfer set necessarily includes a length of medical tubing, including an intermediate segment positioned within the cassette adjacent the reaction surface. This length of medical tubing includes a patient end releasably connectable to an indwelling peritoneal dialysis tube and an opposite end releasably connectable to an assembly for containment of dialysate solution.

Most notably, this invention provides a method of performing a peritoneal dialysis procedure on a patient which permits that patient to remain ambulatory during infusion and evacuation of dialysate solution. The method comprises the steps of:

1. associating a detachable, disposable peritoneal dialysis transfer set with a portable pumping device. (The transfer set is of the form described in this disclosure to provide a directional flow path for dialysate solution between an indwelling patient catheter tube and a dialysate containment system. The portable pumping device may be any of those described in this disclosure.)

2. The transfer set, pumping device and dialysate containment system are all shaped and dimensioned so that they are suitable for attachment to a patient for ambulatory transport by the patient during infusion and exhaustion of dialysate solution.

3. operating the portable pumping device to infuse peritoneal dialysate solution from the dialysate containment system to the patient;

4. waiting for a period of time sufficient to allow dialysis within the patient;

5. operating the portable pumping device to evacuate the dialysate solution from the peritoneal cavity of the ambulatory patient to the dialysate containment system; and 6. disassociating the transfer set from the pumping device to enable disposal of the transfer set and the dialysate containment system.

Circuitry means for selectively governing actuation, direction and operation of the motor are preferably also included. The circuitry may comprise sensor means for detecting pressure changes based upon changes of rotational rate per time interval of the drive shaft or turn shaft. The circuitry may further comprise means for intermittent pump reversal in a selected pattern, said pattern based upon time intervals, external events such as pressure changes or changes in pump speed, or preselected programming. Certain embodiments utilize electronic circuitry to enable regulated flow rates in alternate directions of flow in a net-suctioning pattern. This mode of operation assists in the prevention of obstruction of a suction catheter, for example; particularly at its tip.

Accordingly, a novel method of performing a peritoneal dialysis procedure on a patient who may be ambulatory not only during dialysis but also during infusion and evacuation of a dialysate is disclosed. The novel method comprises the steps of associating a portable peristaltic pump with a detachable, disposable peritoneal dialysis transfer set, said transfer set including an encasement; a tube, a middle portion of which is locatable within the encasement, including check valve means in fluid communication with said tube for preventing passage of air bubbles and particles as a dialysate solution is pumped through the check valve means toward the peritoneal cavity of the patient and for allowing free, at least largely unfiltered flow of the dialysate solution away from the patient; operating the portable pump to infuse peritoneal dialysate solution from the dialysate containment system through the patient end and releasably connected indwelling tube to the patient; optionally temporarily disassociating the portable pump from the transfer set without disconnection of the patient end from the indwelling peritoneal dialysis tube; waiting for a period of time sufficient to allow dialysis within the patient; reassociating the optionally disconnected portable pump to the transfer set; operating the portable pump to evacuate the dialysate solution from the peritoneal cavity of the ambulatory patient to the dialysate containment system; and disassociating the transfer set from the pump to enable disposal of the transfer set and containment system. The containment system of this method may comprise one single-compartment dialysate container. The device remains unobtrusive while enabling ongoing suction of undesired bodily fluids of an ambulatory patient. The micro-evacuator system of the present invention is sufficiently inexpensive to be disposable and sufficiently simple for use in a home care environment and may be equipped with a real-time monitor and indicator of catheter pressure and other important variables.

BRIEF DESCRIPTION OF THE DRAWINGS

In the drawings, which illustrate what is currently regarded as the best mode for carrying out the invention:

BRIEF DESCRIPTION OF THE DRAWINGS

Figure 1:
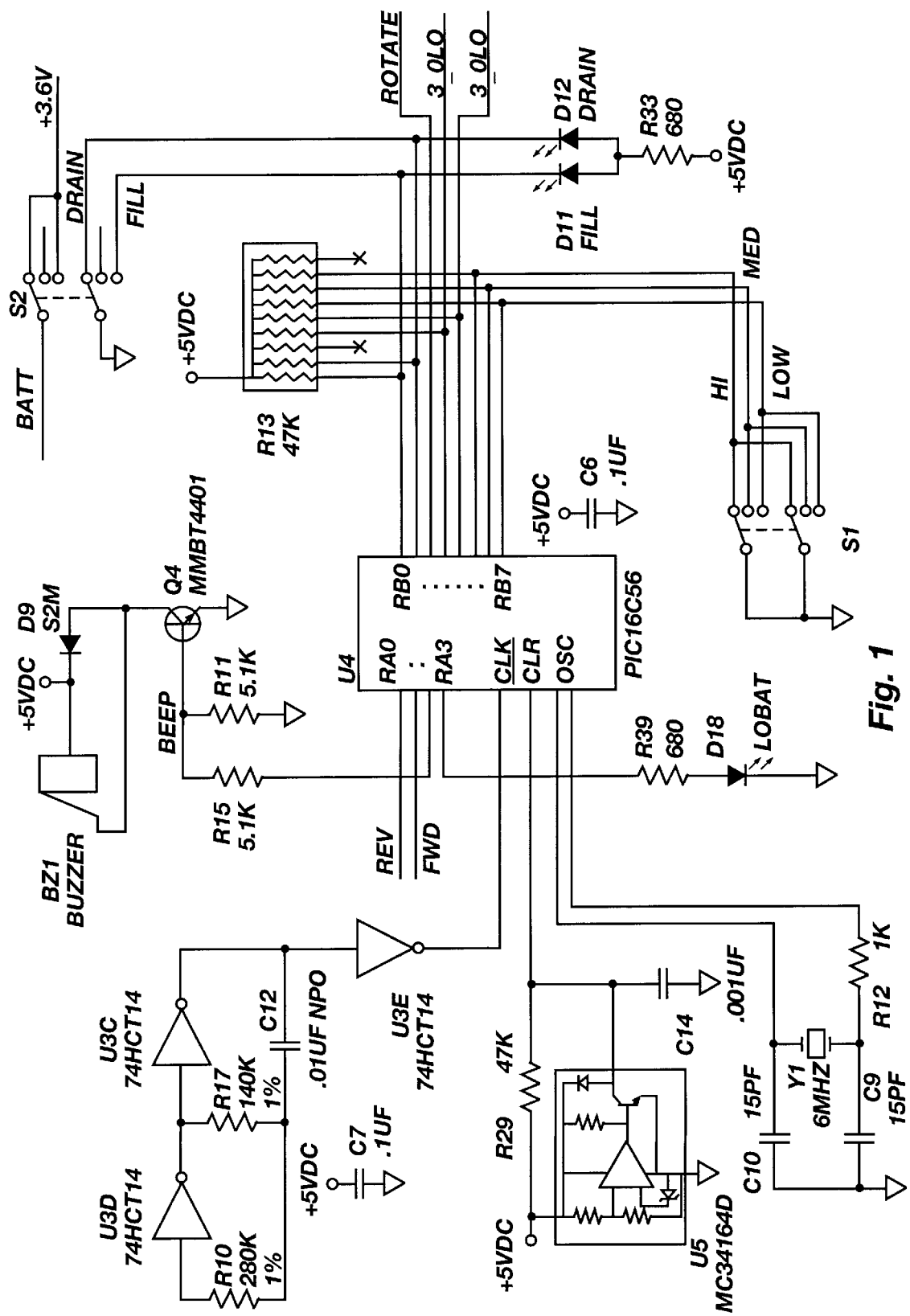

FIG. 1 is a schematic of the circuitry for the central processing unit.

Figure 2:
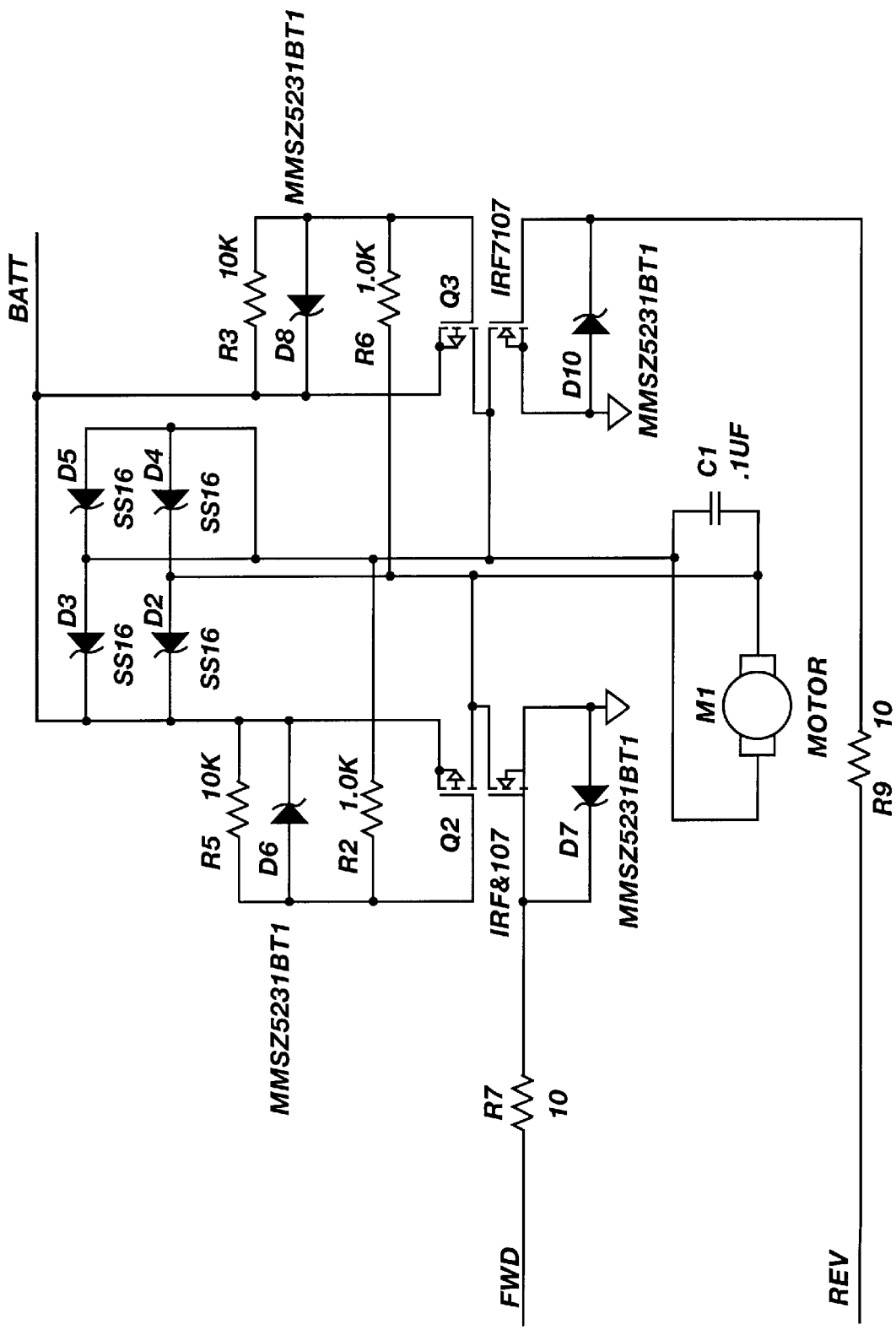

FIG. 2 is a schematic of an H-bridge motor driver circuit.

Figure 3:
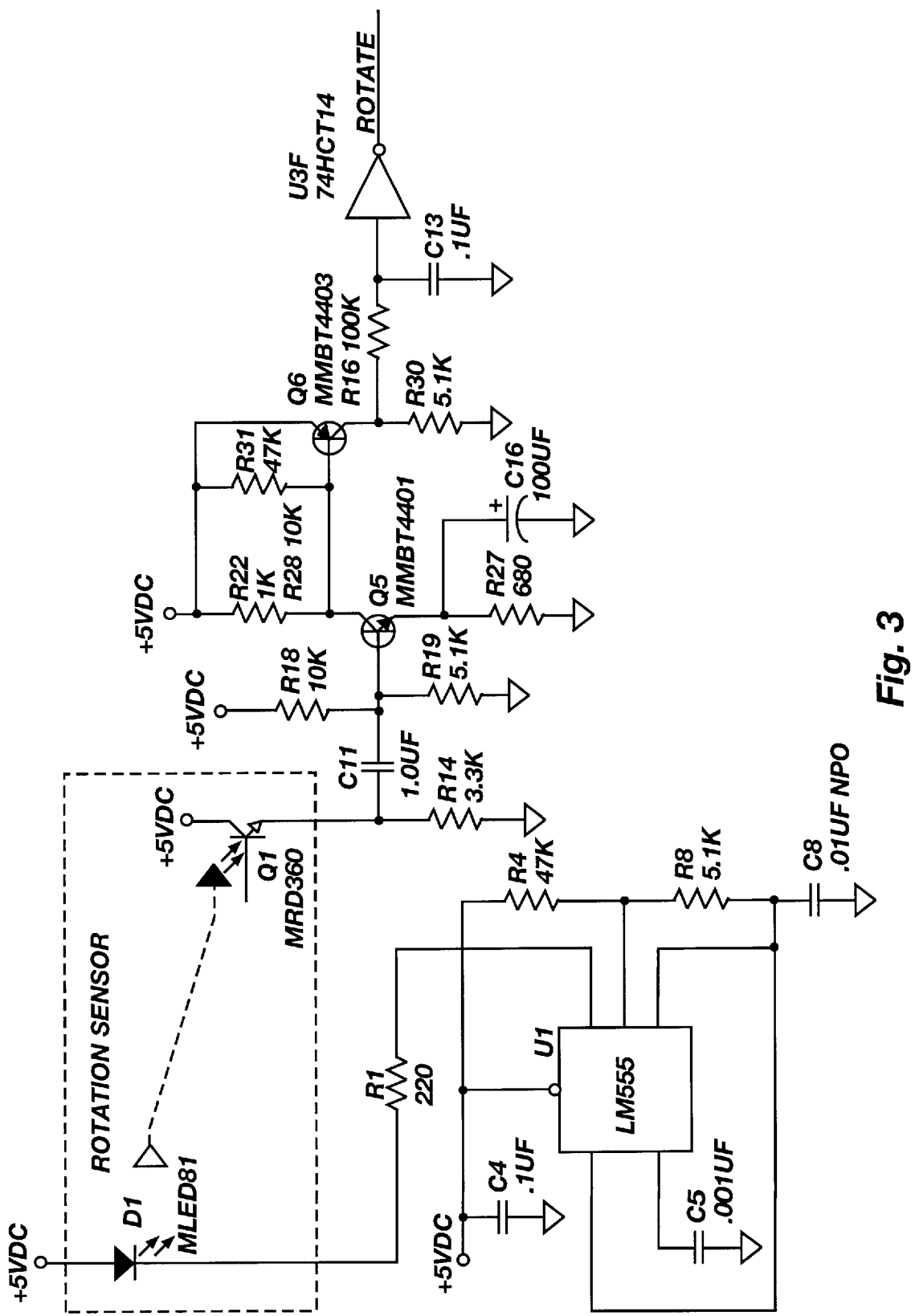

FIG. 3 is a schematic of the circuitry utilizing an infrared detector.

Figure 4:
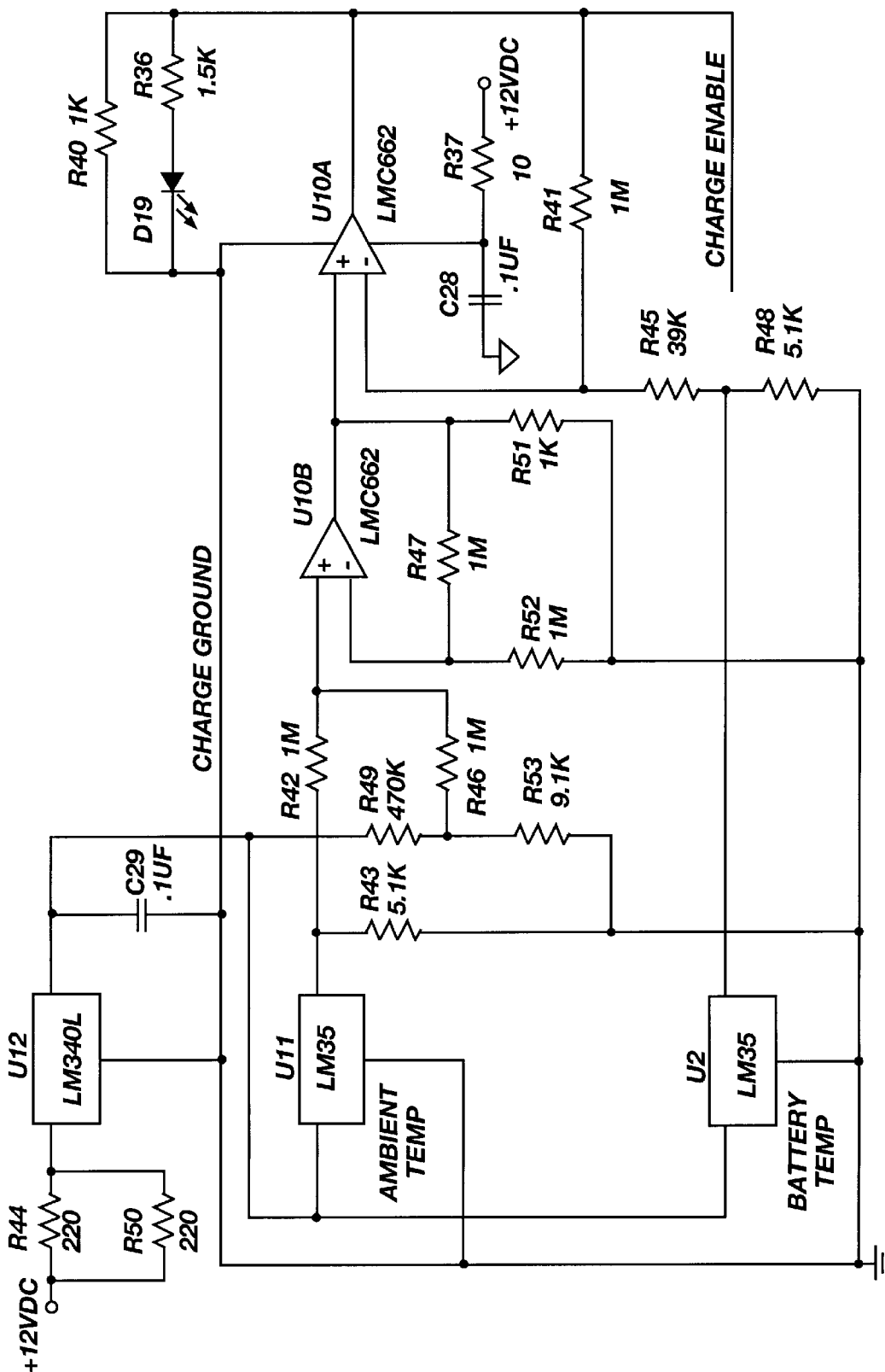

FIG. 4 schematically outlines network circuitry of temperature sensor electronics.

Figure 5:
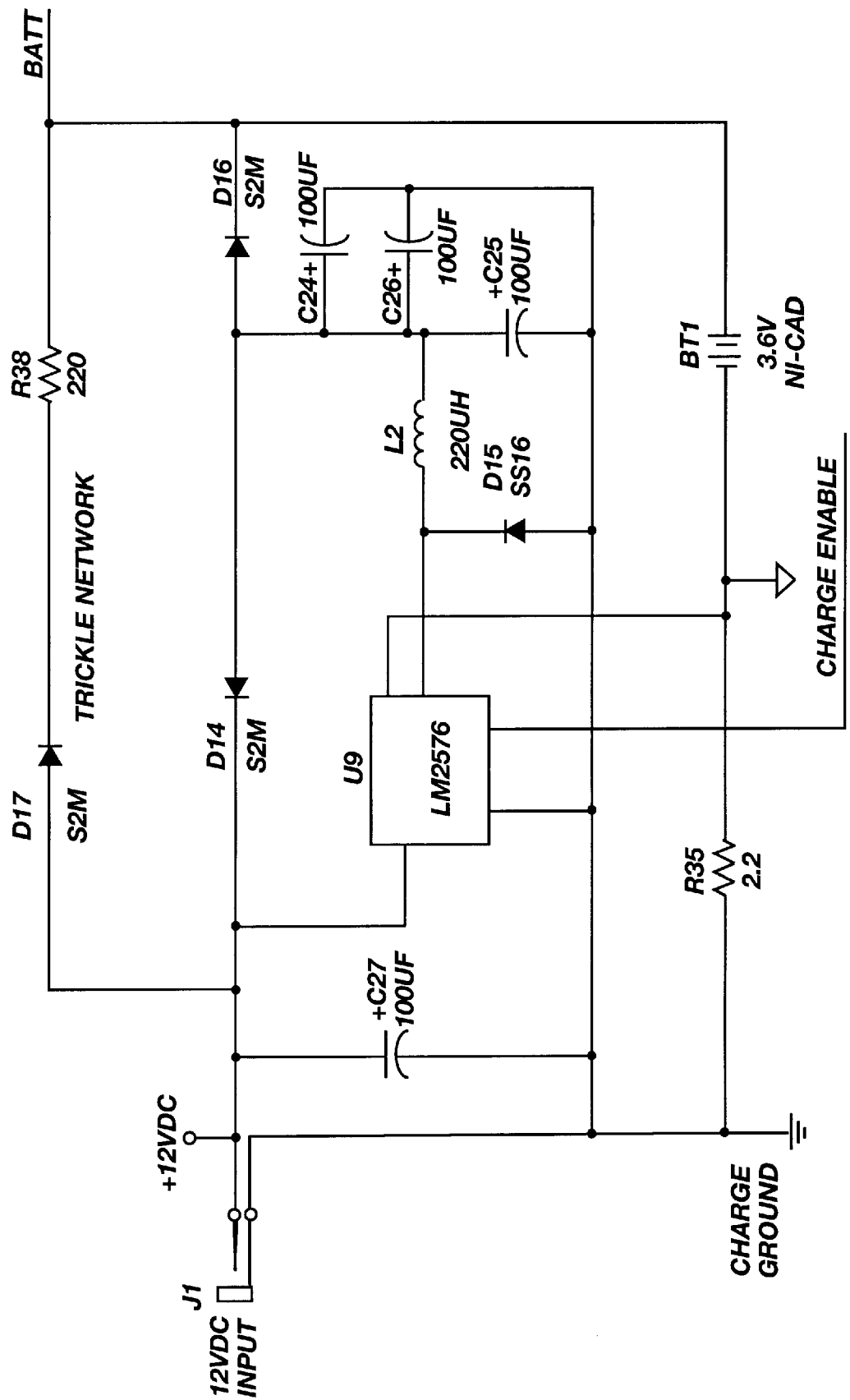

FIG. 5 is a schematic for battery recharging from an external power source.

Figure 6:
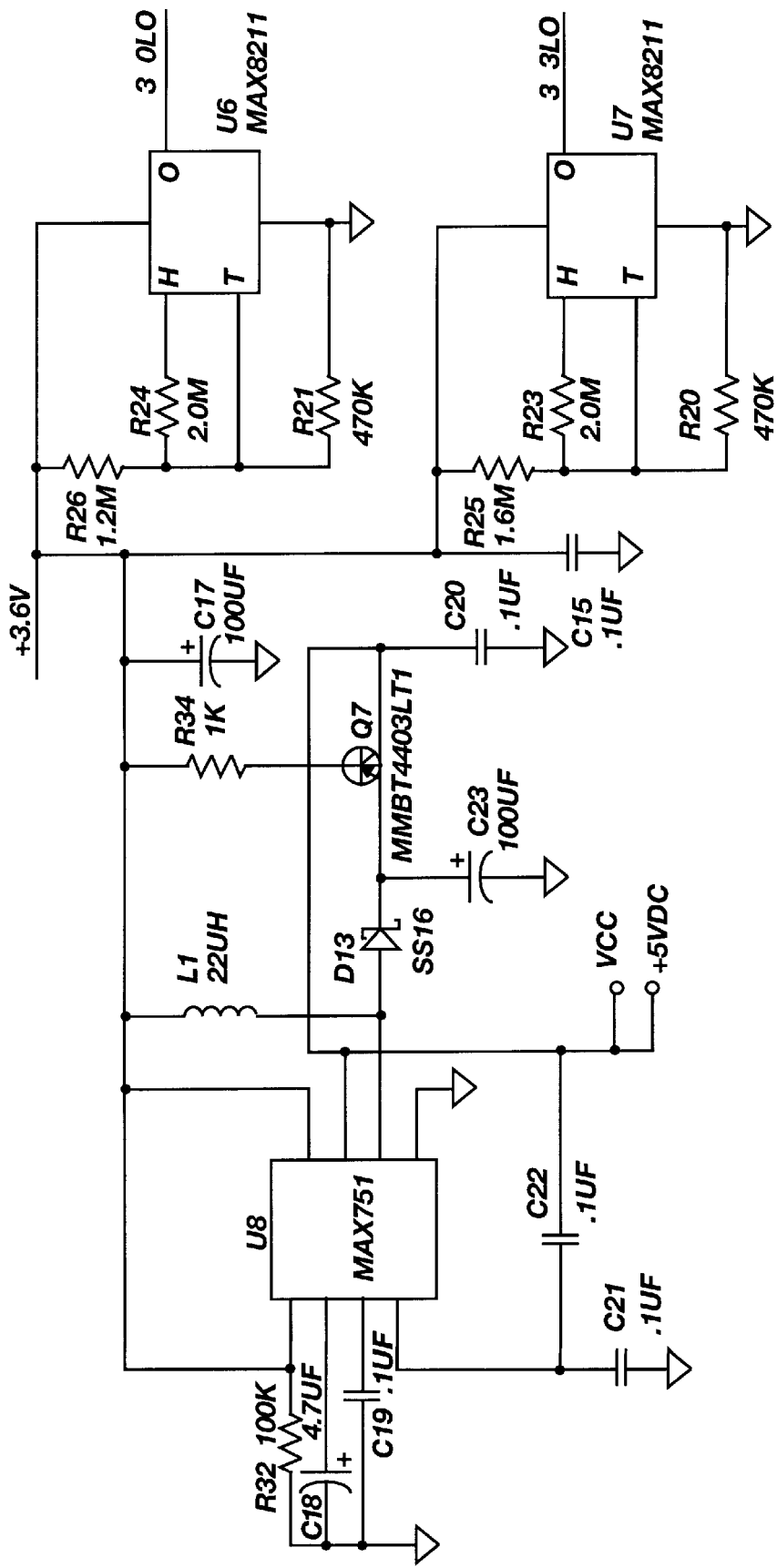

FIG. 6 is a circuitry schematic of the battery monitoring function.

Figure 7:
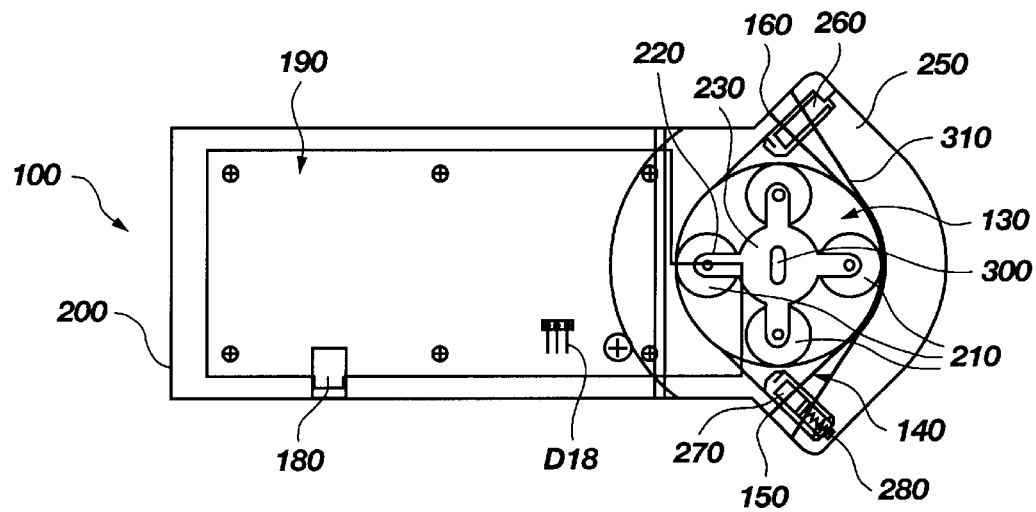

FIG. 7 is a top, partially open view of the peristaltic pump featuring the wheel and spindle assembly, portions of the circuit board and including the transfer cassette.

Figure 8:
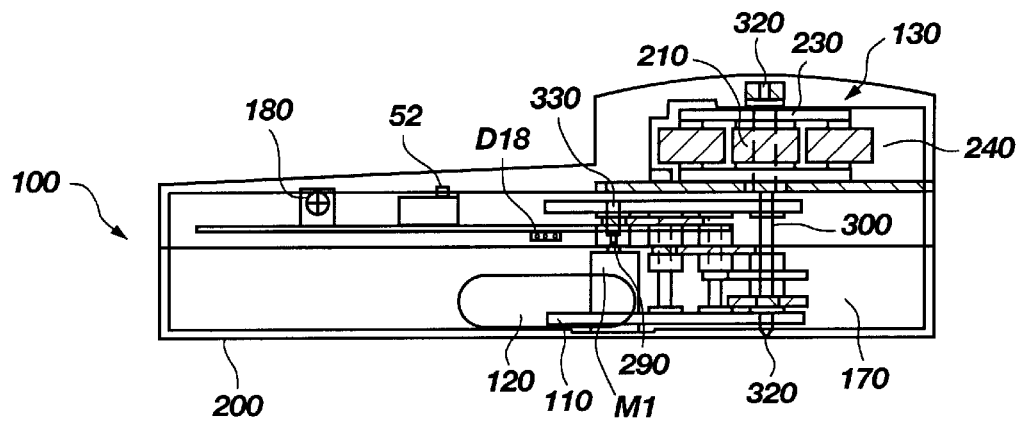

FIG. 8 is a side, partially transparent view of the peristaltic pump without the transfer cassette.

Figure 9:
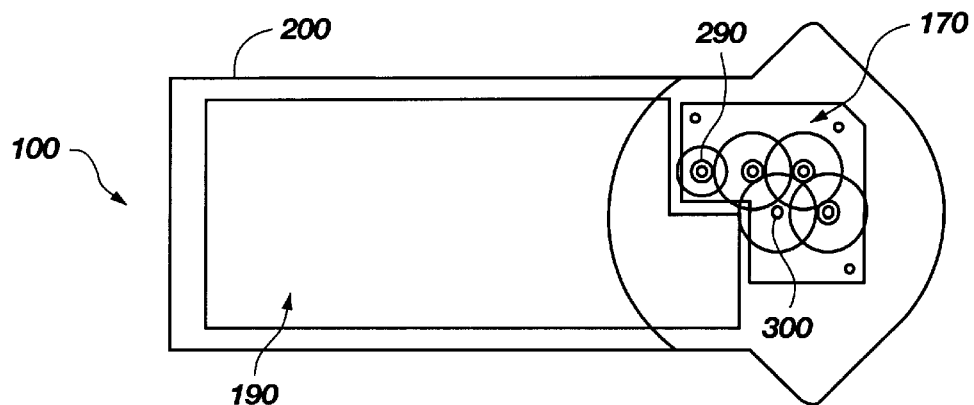

FIG. 9 is a top, partially open view of the peristaltic pump featuring the gear configuration.

Figure 10:
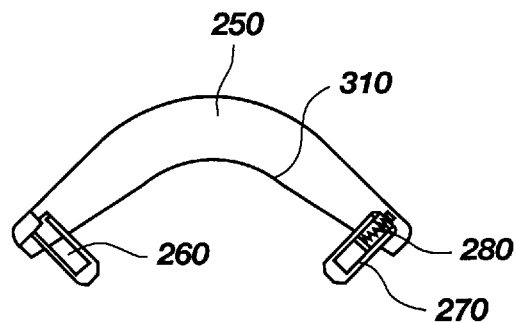

FIG. 10 is a top view of the transfer cassette.

Figure 11:
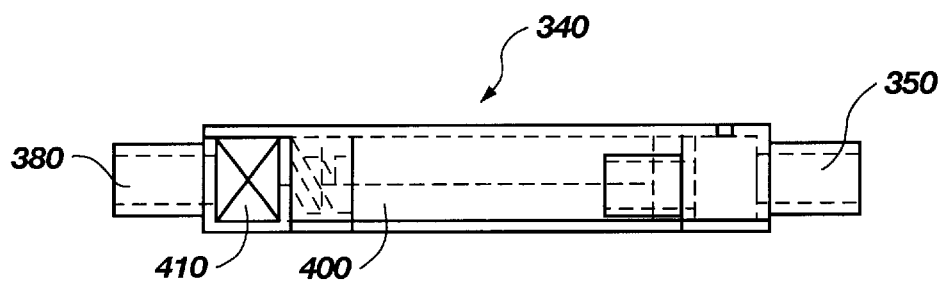

FIG. 11 is a top view of the particle and air filter.

Figure 12:
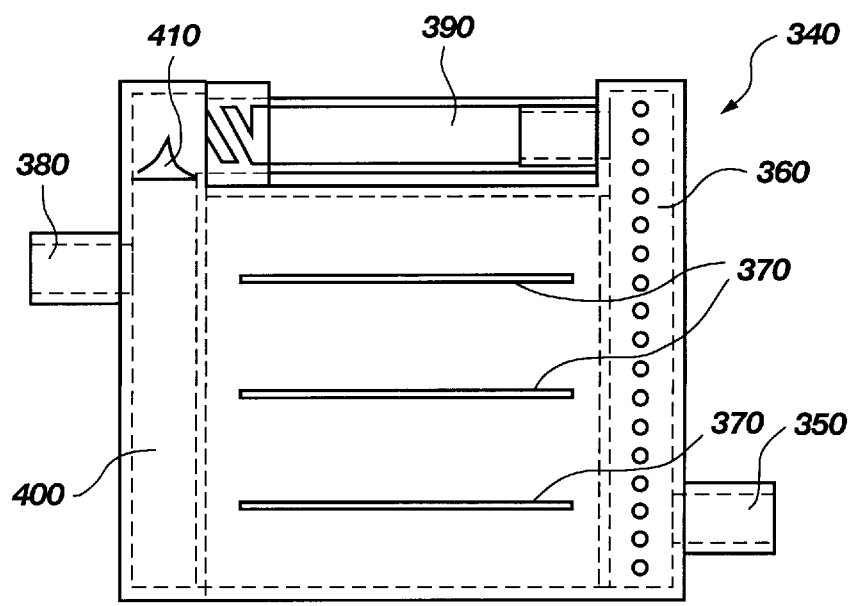

FIG. 12 is a side, partially transparent view of the particle and air filter.

Figure 14:
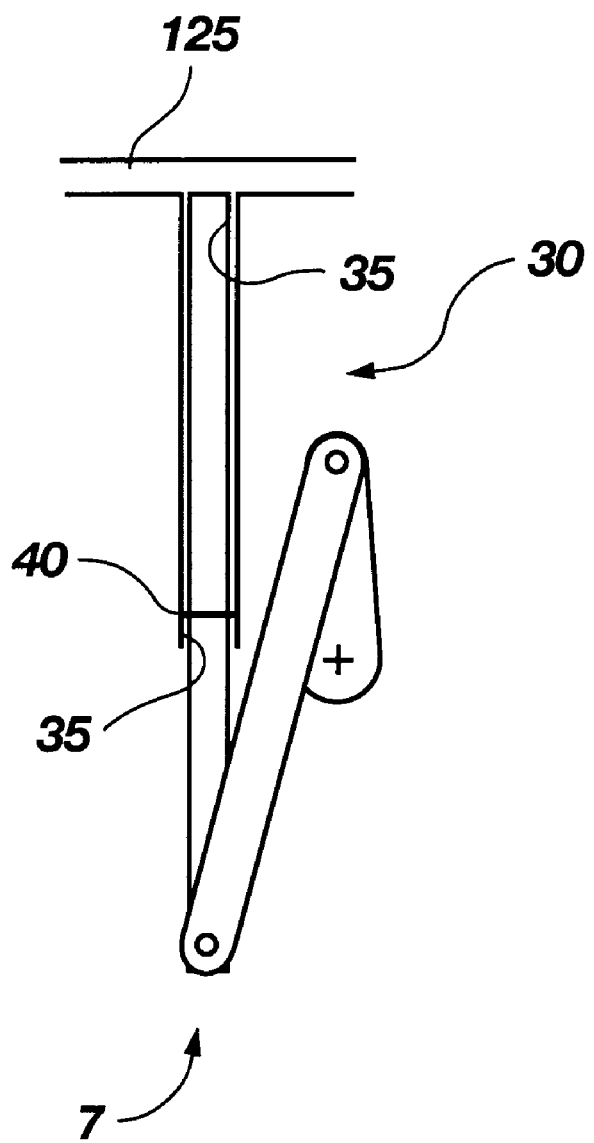
Figure 15E:
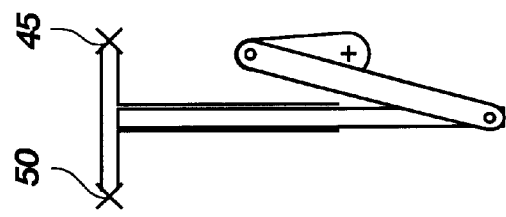
Figure 15D:
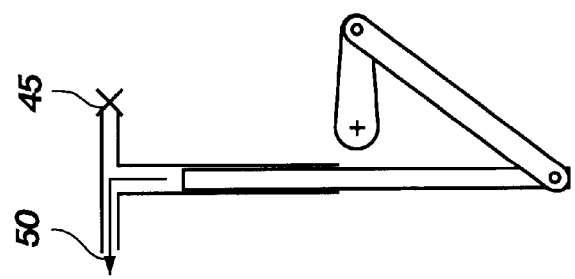
Figure 15C:
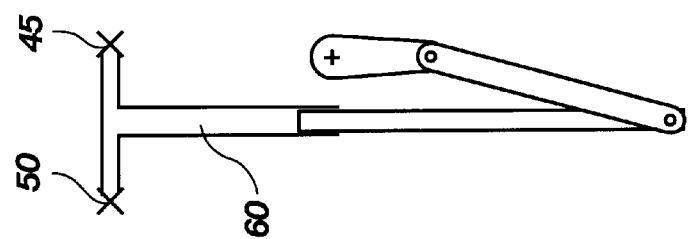
Figure 15B:
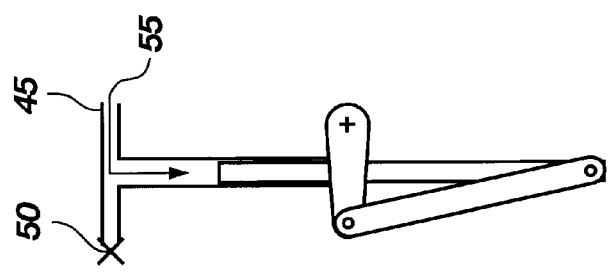
Figure 15A:
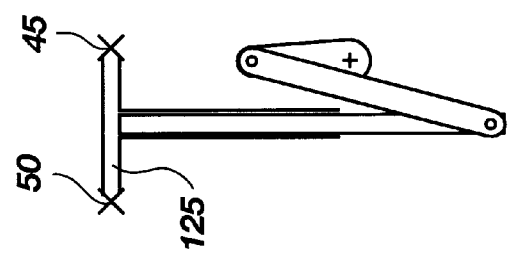
Figure 16A:
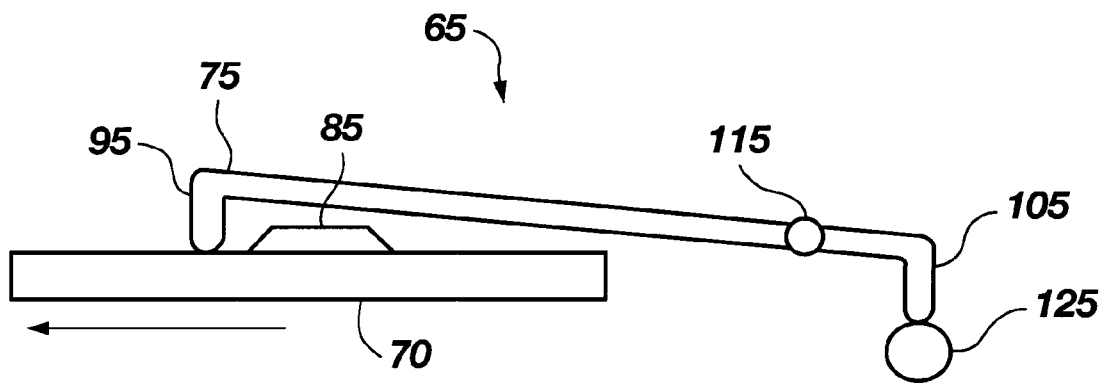
Figure 16B:
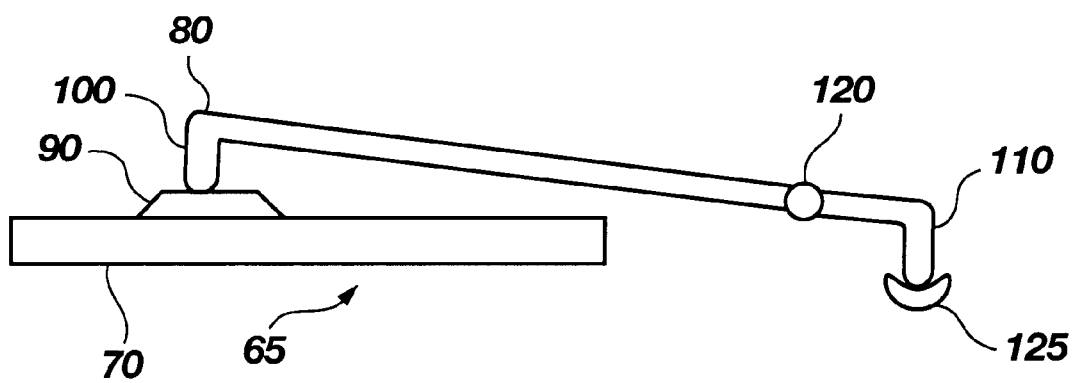
Figure 17:
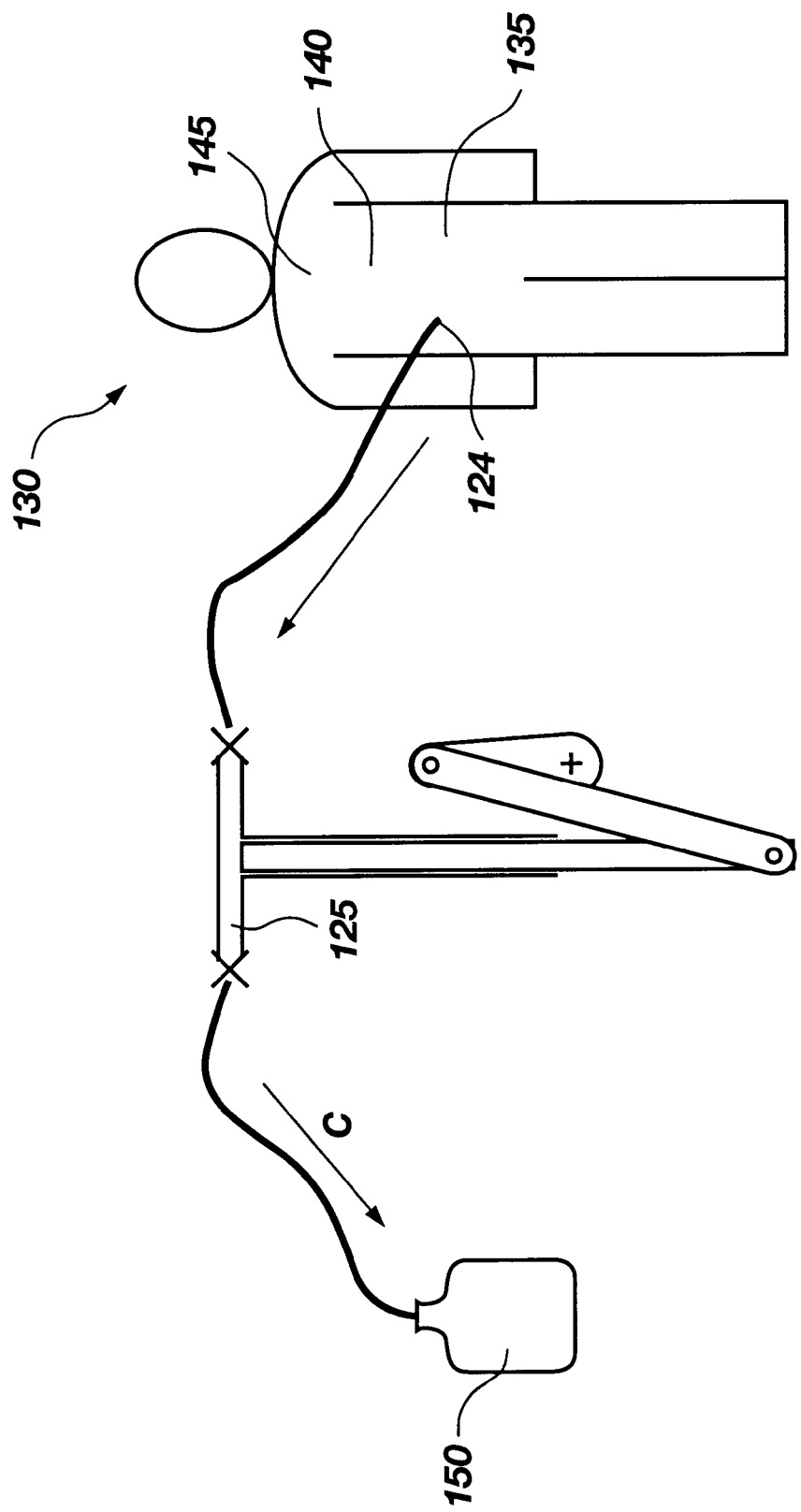
Figure 18A:
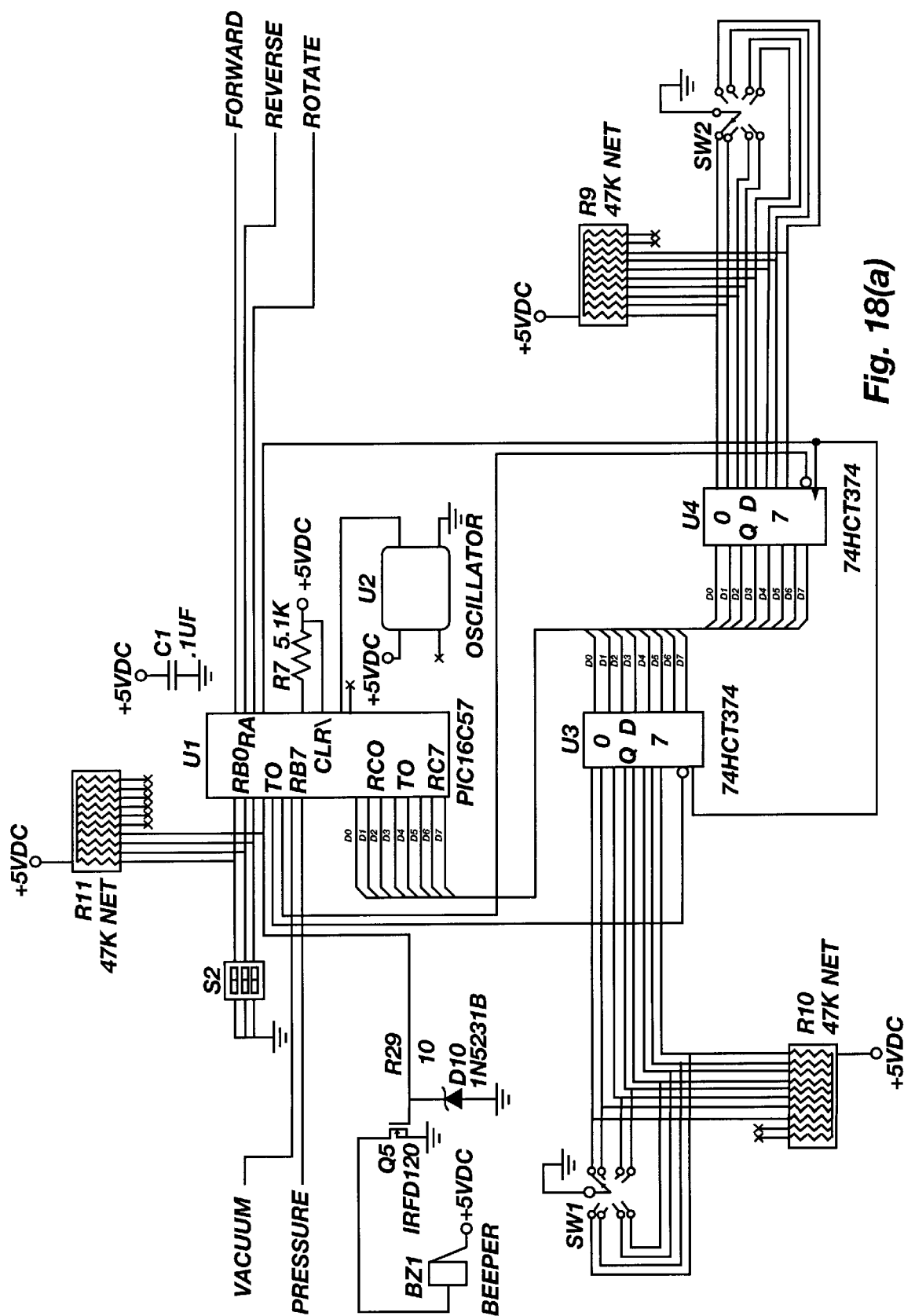
Figure 18B:
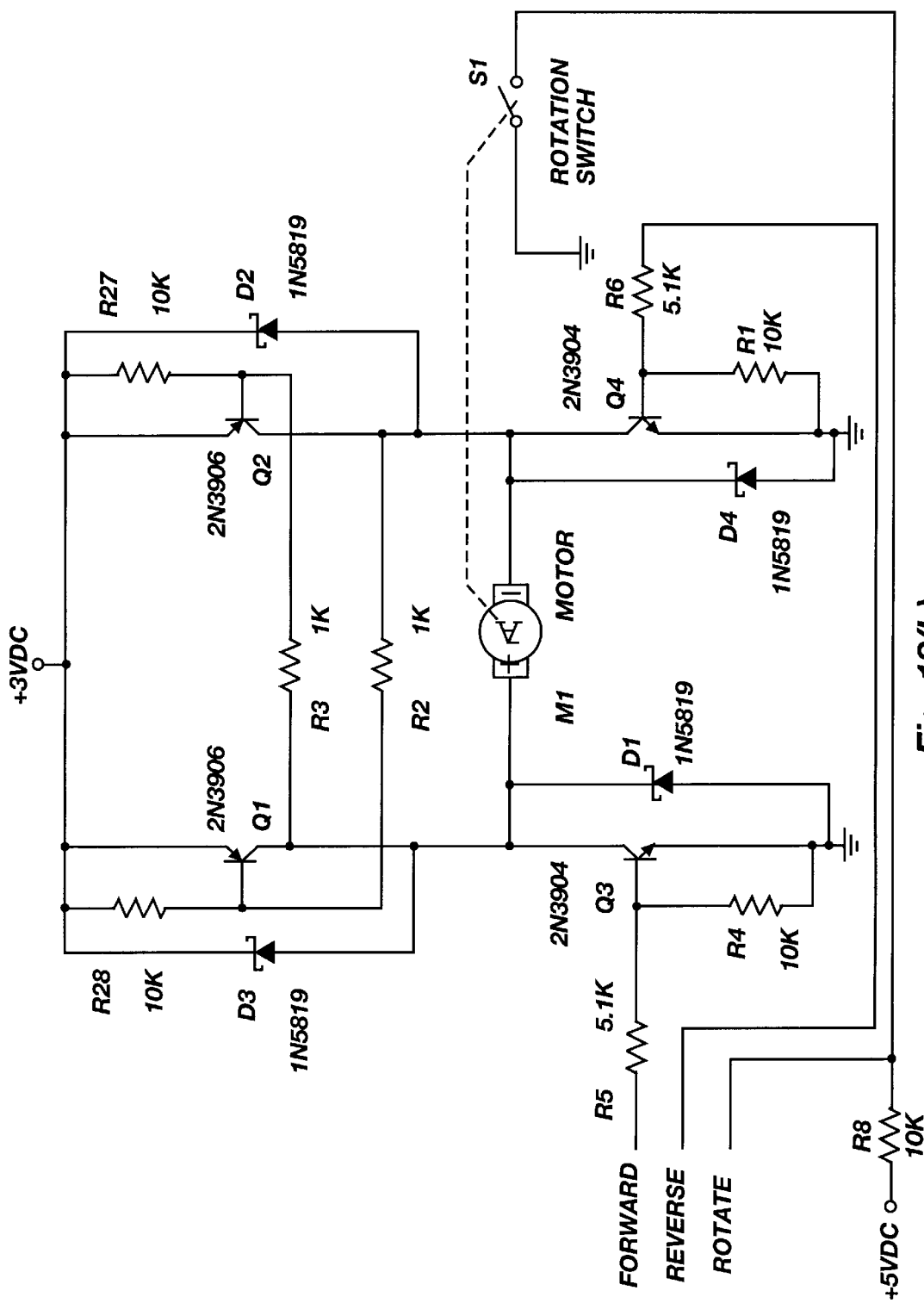
Figure 19:
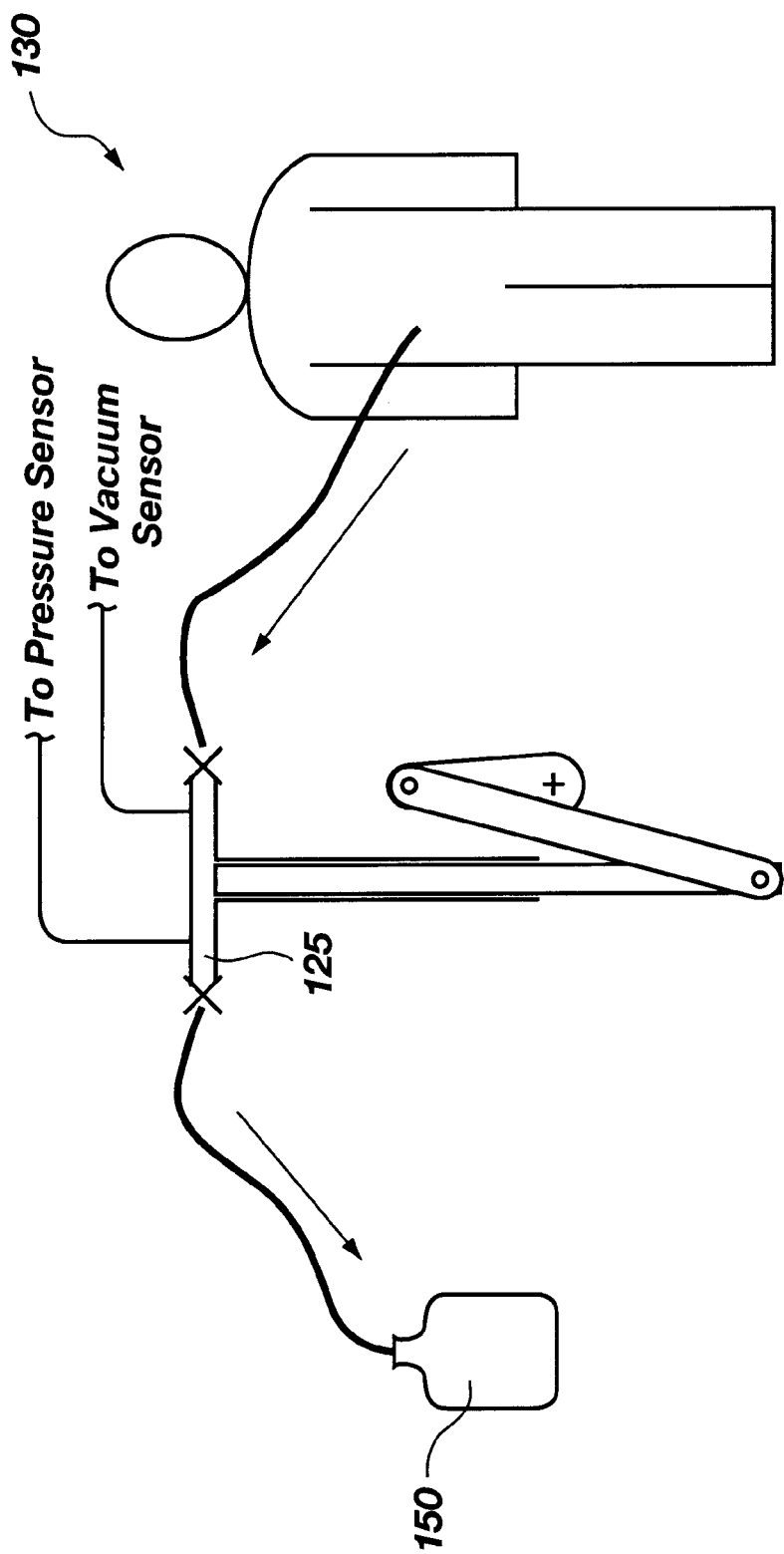
Figure 20A:
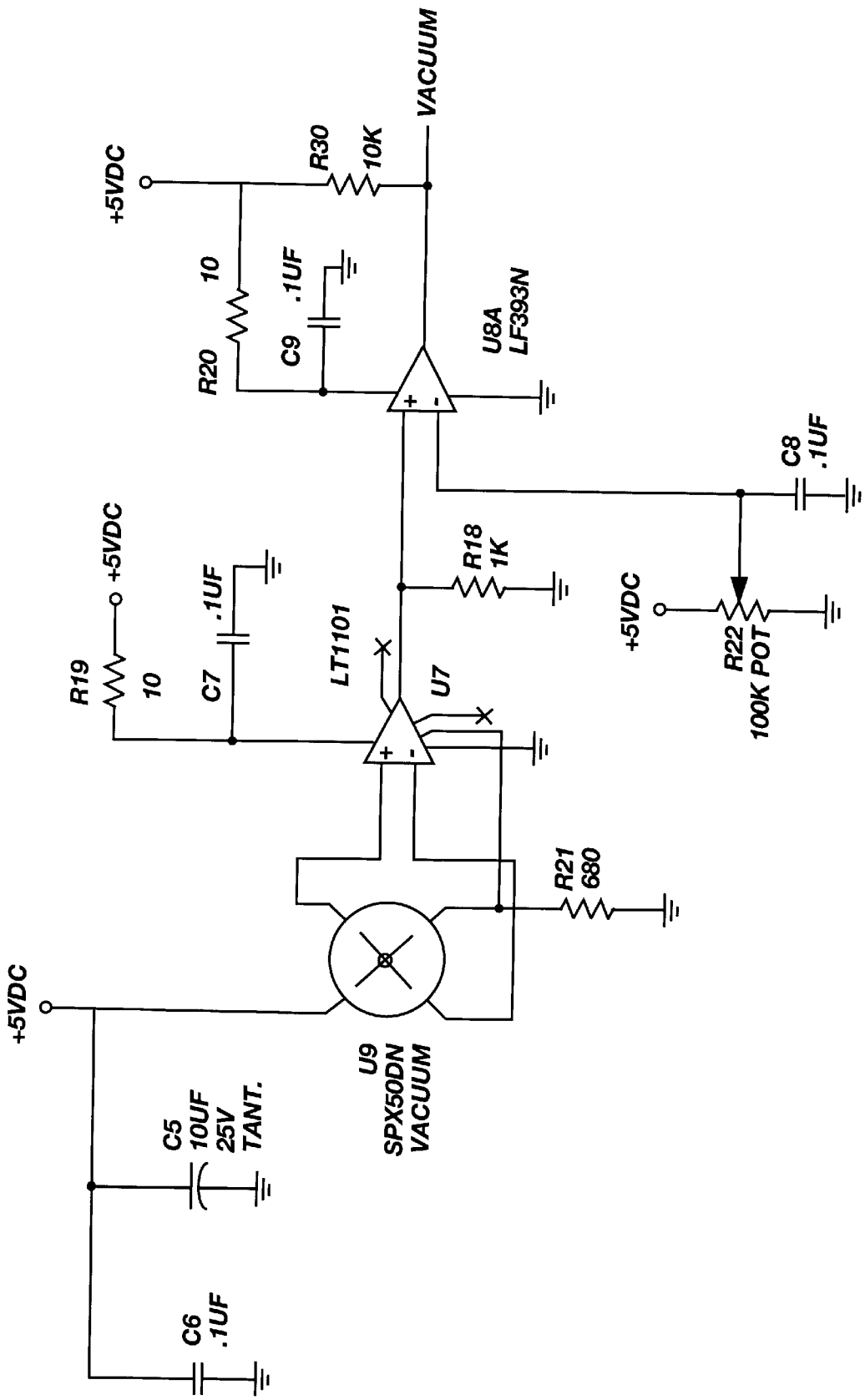
Figure 20B:
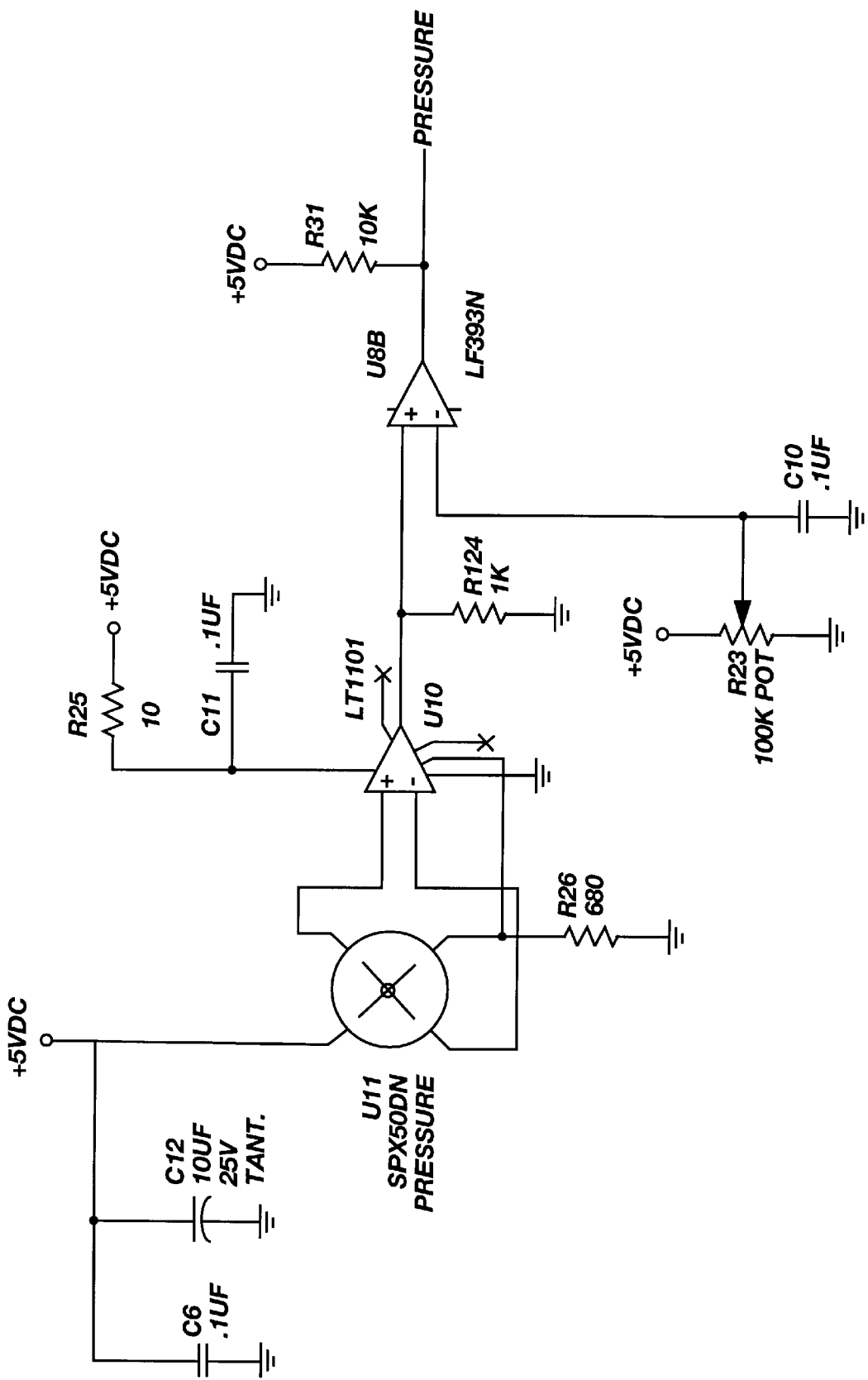
Figure 21A:
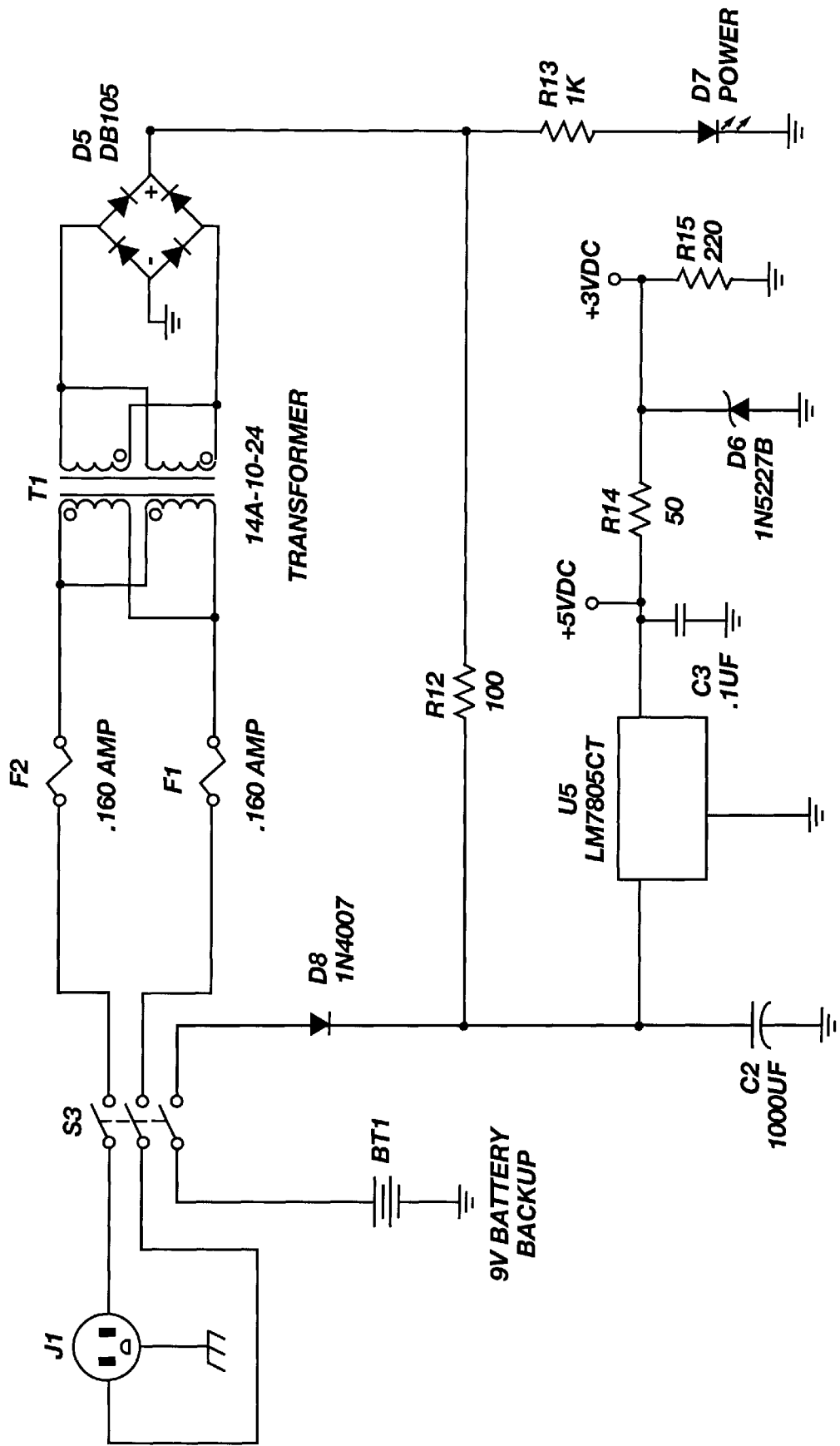
Figure 21B:
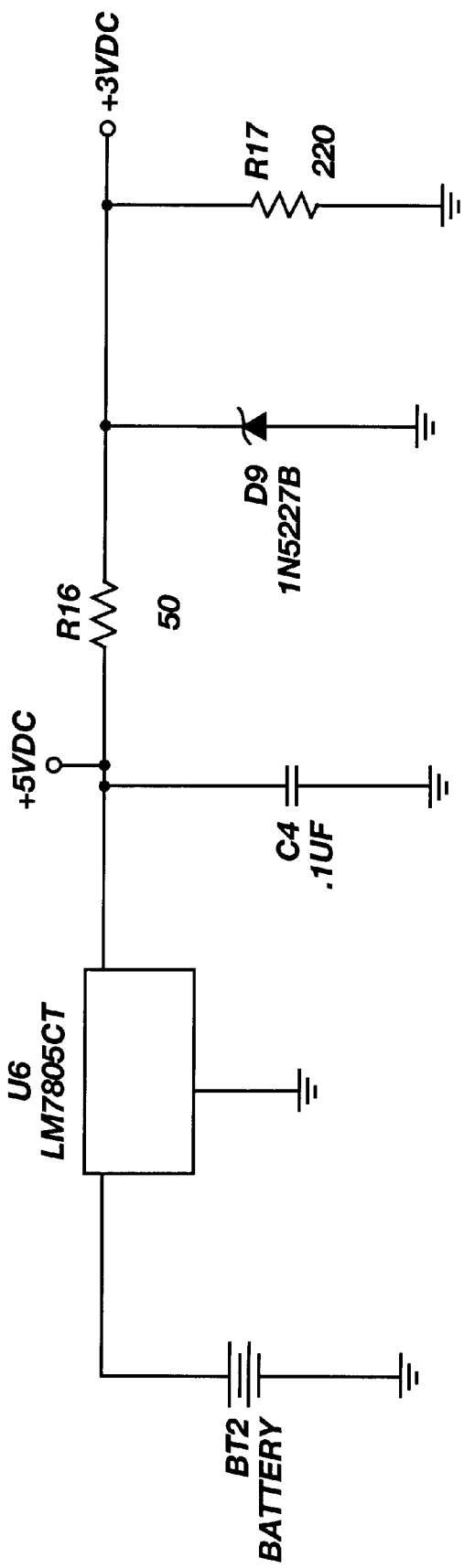

FIG. 13 includes five side views, designated FIG. 13(a) through FIG. 13(e), respectively, illustrating five sequential positions of piston, drive arm and linkage elements during operation;

FIG. 14 is a partial cut away view of the piston seal ring;

FIG. 15 includes five side views, designated FIG. 15(a) through FIG. 15(e), respectively, each partially cut away, illustrating piston positions relative to outlet and inlet valves in the five sequential piston positions of FIGS. 13(a)–13(e);

FIG. 16a is a side view of the cam relative to the lever when the fluid tubing is unobstructed;

FIG. 16b is a side view of the cam relative to the lever when the fluid tubing is obstructed;

FIG. 17 depicts the functional features of the pump system relative to the patient and waste container;

FIG. 18a and FIG. 18b comprise a schematic diagram of a suction control circuit;

FIG. 19 depicts the functional features of the pressure and other sensors relative to the patient and waste container;

FIGS. 20a and 20b compare a schematic diagram of a suction/pressure circuit;

FIGS. 21a and 21b comprise a schematic diagram of a power supply.

DETAILED DESCRIPTION OF THE ILLUSTRATED EMBODIMENT

The electronic circuitry of this invention has several functions, and may be organized as illustrated schematically by FIGS. 1 through 6.

FIG. 1 illustrates a central processing unit (CPU) U4 and associated circuitry. The CPU obtains clock pulses from two sources. Crystal Y1 provides the main clock pulses for CPU program step execution. An oscillator, formed by U3C, U3D and associated components, provides a stable 4 mS square wave to the CPU. This 4 mS square wave is used as a time base reference.

U5 holds the CPU reset on power up, or if the incoming +5 VDC supply drops too low. The MC34164 is a voltage measuring device that drops its output low if the input voltage drops below the internally preset voltage. This low output forces the CPU to reset.

The CPU data lines can be programmed for either input, output, or hi-impedance operation. In this application, the data lines RA0 through RA3 are programmed for output operation, while RB0 to RB7 are programmed for input operation.

The CPU itself contains internal memory which is programmed to execute commands that control the overall function of the pump 100. (See generally, FIGS. 7–10.) When power is applied and the CPU reset line goes high, program execution begins. The CPU then monitors the input lines to see whether to drive the motor 110 forward (when a "Fill" command is detected on switch S2) or reverse (when a "Drain" command is detected on switch S2).

Respective input and output data lines are dedicated to the following respective functions:

RA0: Motor Reverse Command (REV)
RA1: Motor Forward Command (FWD)
RA2: Beeper On (BEEP)
RA3: Low Battery Warning LED (LOBAT)
RB0: Fill Command from Control Switch S2 (FILL)
RB1: Drain Command from Control Switch S2 (DRAIN)
RB2: Rotate data from Rotation Sensor (ROTATE)
RB3: Battery 3.0V Sensor input (3_0LO)
RB4: Battery 3.3V Sensor input (3_3LO)
RB5: Hi Speed Command from Control Switch S1 (HI)
RB6: Medium Speed Command from Control Switch S1 (MED)
RB7: Low Speed Command from Control Switch S1 (LO)

Each of the switch and voltage monitoring inputs are pulled high by resistor network R13. This arrangement allows the CPU input line to be pulled to ground by the device connected to the CPU. The exception to this rule is the Rotate input. It is driven selectively low or high by inverter U3F (FIG. 3).

CPU outputs FWD and REV are connected to an H-bridge motor driver circuit, as shown by FIG. 2. The H-bridge is formed by Q2, Q3 and associated components. When the FWD output from the CPU goes high, the REV output will be forced low, and the N-channel mosfet inside Q2 turns on, providing a ground to one side of the motor M1. This ground is also applied to one side of R6 which pulls down the gate of the P-channel section within Q3. At this time the Q3 P-channel section turns on and provides battery voltage to the other side of the motor M1. This action causes the pump motor M1 to rotate in the clockwise direction.

If the CPU output FWD is forced low and the REV output is placed in a high state, the N-channel mosfet within Q3 turns on and provides a ground to the motor terminal 110 formerly connected to the voltage of the battery 120. This ground is also connected to one side of R2, pulling down the gate of the P-channel section within Q2. Q2 is thereby allowed to place the battery 120 voltage on the other side of the motor M1. The motor M1 will then turn counter-clockwise.

If the CPU forces both FWD and REV outputs low, transistors Q2 and Q3 turn off. The motor M1, having no driving voltages, will coast to a stop. To precisely limit the pump 100 to a single rotation, the motor M1 must be stopped abruptly at the end of the rotation. Briefly changing motor direction, such as from clockwise to counterclockwise, will provide a braking function to the motor M1.

The H-bridge is protected from transient voltages by diodes D2 through D8 and D10.

FIG. 3 shows an infrared emitter (D1) that is positioned on the circuit board appropriately to allow its emitted light to reflect from a mirror and back into a detector (Q1). The rotating wheel/spoke assembly, generally 130, passes through this light path as the pump 100 operates. Whenever the light is interrupted, a signal is sent to the CPU via the wire labeled ROTATE. The signal can be used by the CPU to determine how fast the pump 100 is turning by comparison to the 4 mS clock. It can also be used to determine whether the pump 100 has stopped turning for any reason, such as mechanical or electronic failure.

If, during operation, the tubing, generally 140, on the intake side (either the bag side tube 150 or the patient side tube 160 in a reversible pump 100) becomes occluded, the pump 100 will begin to develop a vacuum within the tube. Because the central portion 165 of the tubing 140 has a thin wall, the vacuum will collapse the portion 165, and the wheel/spoke assembly 130 will no longer have to push the fluid load. In this case, with less load on the entire motor M1 and gear assembly 170, the motor M1 will speed up. The infrared detector/CPU combination can detect this increase in speed and signal the operator either with visual flashes on LED D18 (FIGS. 1, 7 and 8) or by a series of beeps on BZ1.

The infrared signal is generated by applying a square wave, made by U1 and its associated components, to the infrared LED, D1. The square wave turns the LED on and off at a frequency of approximately 2000 Hz. The pulsating light travels to the detector and is fed from that point to an AC amplifier formed by Q5, Q6 and associated components. The reflected light is amplified, sent to an inverter U3F, and on to the CPU for processing.

The CPU filters out the 2000 Hz wave to obtain only the rotation component of the signal. The 2000 Hz wave is used to help reject interference from other infrared sources.

The battery 120 is charged when an external 12 volt DC power source is attached to connector J1 (FIG. 5). This 12 volt supply energizes the "Battery Charged" network in FIG. 4 formed by U2, U10, U11 and associated circuitry. U2 and U11 are temperature sensors that detect battery and ambient temperatures respectively. When both temperatures are the same, the battery charging circuitry is enabled by the output of comparator U10A. As the battery 120 nears its state of maximum charge, its temperature begins to climb. When the battery temperature is 10 deg. C above the ambient, the battery charging circuitry is disabled by the output of U10A and the LED D19 is lit.

U12 provides a regulated +5V to the "Battery Charged" detection circuitry. Battery charging is accomplished, as shown by FIG. 5 when U9 and associated components are enabled by the "Battery Charged" circuit. This circuit forms a switching power supply 180 that provides enough current to fast-charge battery BT1. The circuit can be tailored to deliver more or less charging current to the battery 120, depending on its specification, by adjusting the value of resistor R35.

When the charging circuit is disabled, a trickle charge continually keeps the battery 120 in a state of full charge. The trickle can be left on indefinitely because the trickle current is kept below the limit specified by the battery manufacturer. Trickle charge is provided through diode D17 and limited by resistor R38.

The 12 volt source attached to connector J1 can be obtained from a wall adapter or from an automobile cigarette lighter adapter (neither shown).

FIG. 6 illustrates monitoring of battery condition by U6 and U7 that detect voltages of 3.0 and 3.3 respectively. When the battery voltage, ideally 3.6V, drops below 3.3V the CPU is signaled and causes the LED D18 to come on. When a battery voltage of 3.0V is detected by U6 the CPU is again signaled and the motor M1 is turned off, and cannot be enabled until the battery 120 is charged and the unit has been turned off and back on using S2.

The battery voltage is also applied to a switching power supply formed by U8 and associated components. This supply provides 5 volts to the internal circuitry with the exception of the "Battery Charged" circuit.

The circuitry is integrated on a PC board, generally 190, and associated with the battery 120, motor M1, gear assembly 170 and wheel/spoke assembly 130, all of which are enclosed within a body 200. Adjacent the rotatable spindle 230 and appending plurality of wheels 210 and spokes 220 is an arched opening 240 on the body 200 into which may be releasably seated a transfer cassette 250. The transfer cassette 250 is preferably made of a plastic material for economic disposability.

A safety valve 260, which may be integral with the transfer cassette 250, as depicted in FIG. 10, is structured and arranged to occlude the tubing 140 until released counter to its closed bias prior to operation of the pump. If the safety valve 260 is formed integral with the transfer cassette 250, the valve 260 may be designed to release upon installation of the transfer cassette 250 within the arched opening 240. Accordingly, the safety valve 260 prevents inadvertent and untimely back flow from a patient in the event the transfer cassette 250 is disassociated from the arched opening 240 of the pump 100 to relieve the patient of the pump 100 during dialysis.

A releaseable clip 270 holds the transfer cassette 250 within the arched opening 240. The clip 270 is structured and arranged to preclude unintentional release of the transfer cassette 250; a user may manually unlatch a release pin 280 to disengage the clip 270 and detach the pump 100 from the transfer cassette 250.

The transfer cassette 250 defines a wall 310 against which the central portion 165 of the tubing 140 is resiliently compressed by the plurality of wheels 210 as the turn shaft 300 in operation rotates the spindle 230 and appending wheel/spoke assembly 130 in either direction.

In operation, the battery 120 powers the motor M1, the motor M1 drives a drive shaft 290 at a velocity of between 1,500 and 15,000 rotations per minute ("rpm's") which in turn drives the gear assembly 170. The gear assembly 170 reduces the rpm's from the drive shaft 290 to a turn shaft 300 in a ratio of approximately fifteen to one, enabling the pump 100 to drive volumetric flow rates in excess of 100 ml/minute for at least 20 minutes.

Alternatively, the electrical power drive of the motor M1 and associated gear assembly 170 may be effectively replaced by use of a manual drive handle (not shown) structured and arranged to be attached to the spindle 230 at a manual drive socket 320 situateable at either end of the turn shaft 300. It is also within contemplation that a powered chuck, such as that of a power drill or power screwdriver (not shown), may be coupled (at higher rpm's) to an alternative drive socket 330 or (at lower rpm's) directly to the manual drive socket 320.

In the preferred embodiment of the invention, a check valve 340 is interposed along and in communication with the liquid flow channel comprising the tubing 140 and preferably located near the patient on the patient side 160 of the tubing 140. The check valve 340 depicted in FIGS. 11 and 12 is structured and arranged to filter air and particles from the dialysate solution as it flows toward a patient and to allow free, unfiltered flow of dialysate solution away from a patient.

The check valve 340 comprises a supply port 350 into which flows unused dialysate solution; an air passage 360; a pre-flow chamber 365 where air bubbles and excess air entering the check valve 340 may be collected for exhaustion through the air passage 360; hydrophilic filter media 370 capable of screening air bubbles and particles of 0.2 micron size and larger from the dialysate; a disposal port 380 through which unused dialysate solution can continue to the peritoneal cavity of a patient or through which used dialysate can be evacuated from a patient; an after-flow chamber 390 in fluid communication with the disposal port 380; and a filter bypass 400 providing a route for used dialysate to at least partially circumvent the filter media 370. Second valve means 410 may optionally be included to ensure that used dialysate substantially entirely circumvents the filter media. Such means 410 may beneficially be in communication with the disposal port 380 and after-flow chamber 390.

The check valve 340 may desirably be structured in a wafer-like shape, as illustrated, to facilitate unobtrusive storage against the body of a patient. Such storage makes feasible patient comfort as well as inconspicuous association with the indwelling incubation apparatus for potential repeat use throughout a series of dialysate transfers. The indwelling tube and peritoneum are thereby protected significantly from microbial contamination throughout multiple transfers and during the interim when, for example, a dual bag system is detached during CAPD.

EXAMPLE 1

This example describes a low volume evacuation system constructed in accordance with FIGS. 13 through 21b of the drawings.

Views (a)–(e) of FIG. 13 illustrate five positions of a pump piston assembly 7 and three of its main components. FIG. 13(a) illustrates a drive arm 10 linked to a motor shaft (not shown) at a rotation point 15. The drive arm 10 is attached to a piston 20 by means of a linkage 25.

Figure 13E:
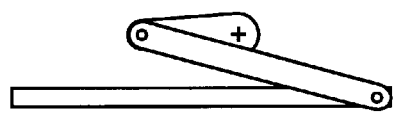
Figure 13D:
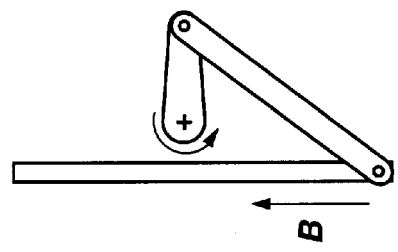
Figure 13C:
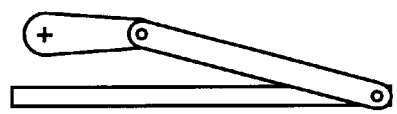
Figure 13B:
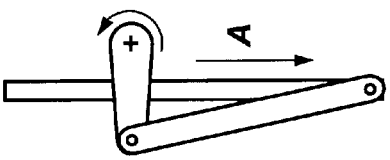

As the drive arm 10 rotates counterclockwise to the position shown by FIG. 13(b), the drive arm 10 and linkage 25 draw the piston 20 downward, in the direction indicated by the arrow A. As the drive arm 10 continues to the position of FIG. 13(c), the piston 20 moves downward to fall extension. Continuing the movement of the drive arm 10 counterclockwise to the position of FIG. 13(d) reverses the direction of piston travel; i.e., the piston 20 is pushed upward, in the direction indicated by the, arrow B, by the linkage 25 until it has reached it full upward movement, as shown by FIG. 13(e), completing one complete travel cycle. If the drive arm 10 continues its counterclockwise movement, the cycle repeats.

Figure 13A:
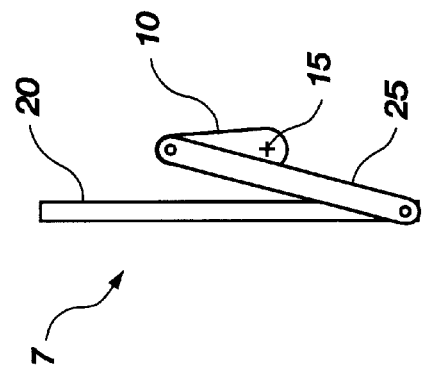

If the piston 20 is placed within a cylinder 30 as shown in FIG. 14, such that there is a seal between the piston 20 and the walls 35 of the cylinder 30, the action of the operating piston 20 will create either a vacuum [FIGS 13(a)–13(c)], within the cylinder 30, or pressurize the cylinder 30 [FIGS. 13(c)–13(e)]. The vacuum or pressurization can be sustained by a seal ring 40 or by a tight fit between piston 20 and cylinder 30.

FIGS. 15 (a)–(e) illustrate the basic function of two valves 45,50 attached to the cylinder 30 and piston 20. FIG. 15(a) illustrates valves 45,50 closed. As the drive arm 10 begins to turn in a counterclockwise direction, an inlet valve 45 is opened allowing fluid 55 to enter the chamber 60 due to the vacuum created by the piston 20, as shown by FIG. 15(b). Fluid 55 continues to flow into the cylinder 30 until the piston 20 reaches its maximum downward stroke, as shown by FIG. 15(c), at which time the inlet valve 45 is closed. As the drive arm 10 continues its counterclockwise travel, the piston 20 begins to move forward to create pressure in the cylinder 30 [FIG. 15(d)]. An outlet valve 50 is then opened to allow the movement of fluid 55 out of the cylinder 30 until the piston returns to its initial position [FIG. 15(e)].

FIGS. 16a and 16b illustrate a gear mechanism 65 attached to the motor (not shown) which includes a cam 70 that rotates one time per complete piston cycle. This cam 70 is linked to the valves 45,50 by means of two levers 75,80, one for each valve 45,50, that ride upon the cam 70 as it rotates. Protrusions 85,90 are placed on the cam 70 such that they engage the levers 75,80 when the piston 20 is in the correct position. The levers 75,80 turn the valves 45,50 on and off as they encounter a protrusion 85,90 on the cam 70. The levers 75,80 could include wheels or other friction-reducing components that ride upon the cam 70.

The levers 75,80 each comprise a cam end 95,100 and a tube end 105,110. As the cam end 95 of one of the levers 75,80 upwardly encounters one of the protrusions 85,90, the lever 75 or 80 pivots around the particular one of the pivot points 115,120 associated with the one of the levers 75,80. As the lever 75 or 80 thus pivots, its corresponding tube end 105,110 is pressed downward, crimping the tube 125 until the tube 125 is occluded.

Thus, the opposite end of each lever 75 or 80 is placed against the tube 125 attached to either the inlet valve 45 or the outlet valve 50 of the cylinder 60. When the lever 75 or 80 is pressed against the tube 125, and the tube 125 flattens, the internal cross-sectional area through which fluid normally passes is reduced to essentially zero, closing the particular valve 45 or 50. When the lever 75 or 80 is not pressed against the tube 125, the tube 125 resumes its original shape, and maximum cross-sectional area, and the given valve 45 or 50 is open. When all components are working together, a pumping action is produced that will move fluid from inlet to outlet.

Thus far, the drive arm 10 has been described as being rotated counterclockwise. If the motor (not shown) is reversed, the direction of the drive arm 10 changes to clockwise which reverses the sequence shown in FIG. 15. Also, the valve-controlling cam 70 works in reverse. As a result, the functions of the valves 45, 50 are reversed. That is, fluid comes in through the outlet valve 50 and out through the inlet valve 45.

The basic pump system is illustrated in FIG. 17. The pump 7 can be attached to any patient 130 location such as into the peritoneal cavity 135, the pleura 140 or within the bronchial tube 145 using existing entry devices and tubing couplers (not shown). The pump 7 can also be used to remove fluid 55 from external sites such as wounds in the Emergency Room (not shown). As illustrated, fluid 55 is removed by the pump 7 from the patient 130 and deposited into a waste container 150.

Because the pump 7 can be reversed simply by reversing the motor (not shown), it is possible to pump inward (in the direction indicated by arrow C) two or more cycles and then back to the patient 130 one or more cycles. This action ensures that the end 124 of the tube 125 inserted into the patient 130 does not become occluded; pumping back to the patient 130 forces any debris or coagulated fluids 55 away from the end of the entry device or tubing 125. The number of cycles pumped inward as opposed to the number of cycles pumped back to the patient 130 is determined by adjusting appropriate control devices (not shown). To achieve a removal of fluid 55, the number of cycles inward must exceed the number of cycles outward (toward the patient).

A further variation is to change the speed of the motor and thereby the cycle repetition rate to remove either more or less fluid 55 from the patient 130 site per unit of time. Motor speed may also be determined by setting appropriate control devices.

Different pump mechanisms 7 can be manufactured to satisfy the demands of varying applications. For example, the diameter of the pump piston 20 and corresponding cylinder walls 35 can be modified to affect pressure or fluid displacement per cycle.

The pump mechanism 7 may be constructed of disposable materials that enable the parts that have been contaminated by fluids 55 to be discarded. The reusable pump motor and electronics are a separate assembly and are able to be reset and reused. The disposable pump assembly 7 can be sterilized and attaches either by snap fit or by mechanical fastener to the pump motor assembly.

Referring to the suction control schematic diagram of FIG. 18A, the microprocessor (U1) and associated components perform all control and monitoring functions. It is coupled to the motor driving circuitry formed by Q1–Q4 and its associated components. This electronic circuitry called an H-bridge, allows the motor to be driven bi-directionally and has the ability to quickly stop the motor.

When the microprocessor sends a low signal to resistors R5 and R6, both Q3 and Q4 are turned off. Also, the emitter-base junctions of Q1 and Q2 are turned off by resistors R28 and R27, respectively. If the microprocessor sends a high signal to R5, the emitter-base junction of Q3 is forward biased and Q3 turns on. This condition causes current to flow through R3 and consequently forward biases the emitter-base junction of Q2. The action of these two "on" transistors is to provide a ground path from the motor through Q3 and a power supply connection to the other side of the motor through Q2. The motor is thus energized.

If the microprocessor sends a high signal to R6, the emitter-base junction of Q4 is forward biased and Q4 turns on. This causes current to flow through R2 and consequently forward biases the emitter-base junction of Q1. The action of these two "on" transistors is to provide a ground path from the motor through Q4 and a power supply connection to the other side of the motor through Q1. The motor is thus energized, but in the reverse direction. The motor can in this way be controlled by the microprocessor.

If the motor is to be stopped, the microprocessor releases the high signal it had been sending to the H-bridge, which turns the power off to the motor as previously described. The microprocessor then sends a signal to the H-bridge to reverse the direction for a brief period of time. This action causes the motor to come to an immediate halt rather than coast to a stop. Using this technique, it is possible to get one and only one complete pump cycle without any overshoot.

The motor is linked to a rotation sensor (S1) through a gear mechanism that engages the motor shaft. The rotation sensor signals the microprocessor when a single pump actuation has been completed. The rotation sensor can take the form of a mechanical switch, a hall effect device, or optical sensor. Further, the actuating gear could have a small metal plug embedded at one or more points around the circumference while a metal detecting sensor watches for the metal presence. This discussion focuses on a mechanical switch that is activated by a cam on the gear.

Switches SW1 and SW2 are accessible to the operator and allow the device to be controlled according to the needs of the patient. SW1 controls the speed of the motor while SW2 controls the number of cycles of inward pumping as opposed to outward pumping. The setting is expressed as a ratio and has a minimum of 2:1 and a maximum of 100:1. A DIP switch (S2) can be configured by a service person to allow a greater ratio for either the minimum or maximum settings.

The microprocessor loads information from the control switches by means of activating U3 and U4 one at a time. These chips transfer the switch information onto a common data bus that is accessible by the microprocessor. Other selectable functions can be added to the pump simply by adding more switches and data transfer chips. Functions that can be added include, but are not limited to, a delay between pump cycles, or creating groups of pulses, either in an input or output direction, and separated by a time delay.

Power options for the pump unit are shown in power supply schematics of FIGS. 9a and 9b. AC power enters through J1, S3 and fuses F1 and F2. Power is fed from the fuses to transformer T1 where the voltage is stepped down. Bridge rectifier D5 converts the output AC wave into a DC voltage that is filtered by C2. Resister R13 limits current through the "Power On" LED D7. Power from the bridge rectifier is also fed to resistor R12 and onto voltage regulator U5. The output of the voltage regulator is +5 VDC and is high frequency filtered by C3. R12 reduces the power dissipation of the regulator.

The +5 VDC regulator output is further reduced and regulated by the zener diode D6 to +3 VDC. This voltage is fed to the H-bridge for use in driving the pump motor.

The AC power option is equipped with battery back-up that is configured to provide battery power only if the power switch is on and the AC power is not present. Since the motor and circuitry used require minimal power, the battery backup does not need large capacity.

Normally, the voltage coming from the bridge rectifier is higher than the voltage from the backup battery. This reverse biases diode D8. In the event that AC power is interrupted, and the power switch is on, D8 will forward bias and the battery BT1 begins to supply power to the pump.

The "Battery Only" power supply shown in FIGS. 21a and 21b is essentially a duplicate of the AC power supply voltage regulator section with only a battery driving the input. Battery status can be monitored using commercially available integrated circuits. This option is for ambulatory versions that are used by a patient not able to stay in one place or by a patient in a location where AC power is not available.

The voltage regulators shown in the schematic have a relatively high power loss and are given as examples only. Other methods of voltage regulation with higher power efficiencies are available and could as easily be used. These are generally of higher cost, however. One example is the National Semiconductor Simple Switcher series.

To prevent damage to the pump mechanism and extreme pressures delivered to the patient, pressure sensors can be attached to the inlet and outlet tubes as shown in FIG. 19. The electrical diagram of the sensor circuitry is shown in FIGS. 20a and 20b. The output of the circuit is fed back to the microprocessor. When an over-pressure situation is detected, the microprocessor can turn off the pump and notify the operator by means of a beeper, referenced in FIG. 18A.

The pressure sensor U9 is connected to an instrumentation amplifier U7. The pressure signal is amplified 100 times by U7 and relayed to U8A. U8A is configured as a comparator and checks to see if the incoming pressure signal is over or under the specified limit created by potentiometer R22. If the pressure exceeds the limit, then the output sent to the microprocessor goes high and the microprocessor proceeds to shutdown the system. If the pressure is below the limit then the output signal is low and the microprocessor continues on with normal operation.

FIGS. 20a and 20b illustrate a pressure schematic showing two pressure sensor circuits. FIG. 20a is for detection of extreme vacuum or negative pressure. FIG. 20b is for detection of extreme positive pressure. In both cases the same pressure sensor is used. The manufacturer provides different attachment ports depending upon whether positive or negative pressure is being tested.

The pressure sensor manufacturer also offers devices capable of sensing different maximum pressures. A pump device may be manufactured for specific applications that requires higher pressures. In this case a pressure sensor with a higher pressure capability would be selected.

Other methods of detecting pressure problems are available and equally usable. If the pressurized tube is connected to a diaphragm that is attached to a mechanical switch, an extreme pressure will move the diaphragm and actuate the switch. The switch is the device that signals a pressure error to the microprocessor. This method requires no power and would be suitable to a battery powered device.

Reference in this disclosure to details of the illustrated or other preferred embodiments is not intended to limit the scope of the appended claims, which themselves recite those features regarded as important to the invention.

What is claimed is:

1. An apparatus for portable peritoneal dialysis procedures, comprising:
   a transfer set in association with a high-volume peristaltic pump assembly, said pump assembly comprising:
      a portable power supply;
      a motor, powered by said power supply, and including:
         a drive shaft capable of clockwise and counterclockwise rotation;
         a displacement impeller assembly, mounted to turn within an impeller chamber in response to rotation of said drive shaft, and including:
            a plurality of roller elements carried through a circular travel path within said impeller chamber,
            said travel path being situated partially within a zone which presents a receptacle opening into said impeller chamber;
   said transfer set comprising:
      a cassette configured to install within said receptacle opening to occupy said zone, constituting an encasement for a segment of medical tubing, including a reaction surface constructed and arranged closely to approach said travel path when said cassette is installed within said receptacle; and
      a length of medical tubing, including an intermediate segment positioned within said cassette adjacent said reaction surface, said length of medical tubing including:
         a patient end releasably connectable to an indwelling peritoneal dialysis tube; and
         an opposite end releasably connectable to an assembly for containment of dialysate solution.

2. The apparatus of claim 1, wherein said transfer set further comprises:
   a safety valve for selectively permitting flow of a dialysate solution through said length of medical tubing.

3. The apparatus of claim 2, wherein said safety valve is carried by said cassette, and is structured and arranged so that it is normally biased closed and is urged open upon installation of said cassette in said receptacle.

4. The apparatus of claim 1, said pump assembly further comprising:
   a check valve assembly in fluid flow communication with said length of medical tubing, said check valve assembly being structured and arranged to filter air and particles from fresh dialysate solution as it flows toward a patient and to allow free, unfiltered flow of spent dialysate solution away from a patient.

5. The apparatus of claim 1, said pump assembly further comprising:
   electronic control means for said motor, said control means including circuitry for selectively governing actuation and operation of said motor to effect intermittent pump reversal in a selected pattern.

6. In combination, a high-volume, inexpensive, portable, closed system peristaltic pump and transfer set assembly for portable peritoneal dialysis procedures, comprising:
   a motor assembly, including:
      a battery power supply;
      a drive shaft with a velocity of between 1,500 and 20,000 rotations per minute;
      gear means for communicating drive shaft revolutions in a ratio of at least fifteen to one;
      capability to drive volumetric flow rates in excess of 100 ml/minute for at least 20 minutes;
      a spindle including:
         a turn shaft in torque communication with the drive shaft, said turn shaft being located along a central axis of the spindle, the spindle being rotatable in two directions on a plane transverse the axis;
         support structure affixed to and extending radially outward from the turn shaft to a periphery;
         a plurality of wheels, each wheel being rotatable around a respective wheel axis, said wheel axis being transverse the plane;
         said wheels being spaced evenly from each other and connected to the support structure at said periphery; with
   said transfer set comprising:
      an encasement defining a continuous wall and a covering for said spindle, and
      a tube including an intermediate portion positionable along the wall and formed of a biocompatible material, said intermediate portion being collapsible when compressed between said wall and one of said wheels and having a resilient memory against collapse;
      a patient end releasably connectable to an indwelling peritoneal dialysis tube; and
      an opposite end releasably connectable to an assembly for containment and transfer of the dialysate solution.

7. The assembly of claim 6 further comprising:
   a check valve structured and arranged to filter air and particles from the dialysate solution as it flows toward a patient and to allow free, unfiltered flow of dialysate solution away from a patient.

8. The assembly of claim 6, further comprising:
   circuitry means for selectively governing actuation and operation of said motor;
   said circuitry comprising:
      means for intermittent pump reversal in a selected pattern.

9. The assembly of claim 6, wherein said transfer set further comprises:
   a safety valve for selectively occluding and permitting flow of a dialysate solution through said tube.

10. A system for portable peritoneal dialysis transfer procedures, comprising:
    a portable peristaltic pump including:
       battery-powered motor means for rotating a drive chain across a gear assembly to a reduced ratio of rotation;

spindle means rotatable at the reduced ratio of rotation in response to rotation of the drive chain for movement of a plurality of evenly spaced wheels against a resilient, compressible dialysate tube, said tube being seated against a rigid wall, said wall being defined by an encasement, said encasement providing a covering for a portion of said spindle means and for a portion of said tubing, and comprising:
a safety valve structured and arranged to selectively occlude or permit flow of the solution through the tube.

11. The system of claim 10, wherein:
a check valve is interposed along the tube, in fluid communication with the tube, and structured and arranged in combination with a filter to filter air and particles from a dialysate solution as said solution flows toward a patient and to allow free, unfiltered flow of the dialysate solution away from a patient.

12. The system of claim 10, wherein the dialysate tube comprises a patient end releasably connectable to an indwelling peritoneal dialysis tube and an opposite end in fluid communication with one single-compartment peritoneal dialysate container for containment of a dialysate solution prior to flow of the solution toward and after flow from a patient.

13. A transfer set for the exchange of dialysate solution; comprising:
a length of medical tubing constituting a bidirectional flow path for dialysate solution between an indwelling patient catheter tube and a dialysate containment system;
a coupling carried at one end of said length of medical tubing for connection to said catheter tube;
structure in fluid flow communication with said length of medical tubing, said structure constituting means for directing fresh dialysate solution traveling through said tubing towards said coupling through a first travel path and directing spent dialysate solution traveling through said tubing from said coupling through a second travel path;
a biofilter in circuit with said first travel path; and
a check valve assembly in fluid flow communication with said length of medical tubing, said check valve assembly including said biofilter and being structured and arranged to filter air and particles from fresh dialysate solution as said fresh dialysate flows toward a patient and to allow free, unfiltered flow of spent dialysate solution away from a patient.

14. A transfer set according to claim 13, including:
a positive displacement pump in which said length of medical tubing functions as a resilient pump chamber;
said pump chamber being positioned within a housing comprising a support surface for said resilient chamber such that dialysate is urged through said resilient chamber by a traveling roller assembly associated with said housing;
said roller assembly being structured and arranged to press a roller surface against a section of said resilient chamber towards said support surface, whereby to reduce the transverse cross section of said tubing between said roller surface and said support surface, while said roller surface travels away from an inlet to said resilient chamber and towards an outlet from said resilient chamber;
said resilient pump chamber and said support surface being provided in a cassette;
said roller assembly being provided in association with a drive mechanism organized such that said roller surface travels repetitively within an open sided housing from an inlet towards an outlet;
said open sided housing being structured to receive said cassette in an installed condition;
said housing and cassette being mutually adapted so that when said cassette is in said installed condition, said resilient chamber is functionally positioned with respect to said roller assembly; and
a normally biased closed valve being provided in association with said cassette, said valve being structured and arranged to open when said cassette is in its installed condition.

15. A transfer set according to claim 13, including a safety valve for selectively permitting flow of a dialysate solution through said length of medical tubing.

16. In combination, a high-volume, inexpensive, portable, closed system peristaltic pump and transfer set assembly for portable peritoneal dialysis procedures, comprising:
a motor including:
a battery power supply;
a drive shaft with a velocity of between 1,500 and 20,000 rotations per minute;
gear means for communicating drive shaft revolutions in a ratio of at least fifteen to one;
capability to drive volumetric flow rates in excess of 100 ml/minute for at least 20 minutes;
a spindle including:
a turn shaft in torque communication with the drive shaft, said turn shaft being located along a central axis of the spindle,
the spindle being rotatable in two directions on a plane transverse the axis;
support structure or spokes affixed to and extending radially outward from the turn shaft to a periphery;
a plurality of wheels, each wheel being rotatable around a respective wheel axis, said wheel axis being transverse the plane;
said wheels being spaced evenly from each other and connected to the support structure at said periphery;
a transfer set comprising:
an encasement defining a continuous wall and a covering for said spindle, and
a tube including:
an intermediate portion positionable along the wall and formed of a biocompatible material said intermediate portion being collapsible when compressed between the wall and one of the wheels and having a resilient memory against collapse;
a patient end releasably connectable to an indwelling peritoneal dialysis tube; and
an opposite end releasably connectable to an assembly for containment and transfer of the dialysate solution; and
circuitry means for selectively governing actuation, direction and operation of said motor;
said circuitry means comprising sensor means for detecting pressure changes based upon changes of rotational rate per time interval of the drive shaft or turn shaft.

17. The assembly of claim 16, further comprising second valve means for ensuring that used dialysate substantially entirely circumvents the filter media.

18. A system for a portable peritoneal dialysis transfer procedure, comprising:
a portable peristaltic pump including:

a battery-operated motor, comprising:
- a drive shaft,
  - gear means for communicating drive shaft revolutions in a reduced ratio, and capability to drive flow rates suitable for peritoneal dialysate transfer;
  - a spindle rotatable on a spindle plane in ratio-reduced response to operation of said motor, wherein a plurality of wheels is rotatable on a plane non-perpendicular to the spindle plane, said wheels being spaced evenly from each other and affixed to a support structure said support structure appending from the spindle;
  - an encasement defining a wall;
  - a transfer tube releasably connected to and in fluid communication with an indwelling peritoneal dialysis tube at a patient end of said transfer tube, an intermediate portion of the transfer tube resiliently collapsible when compressed between the wall and any of said wheels;
- circuitry means for selectively governing actuation and operation of said motor;
- a check valve interposed along the tube, in fluid communication with the tube, and structured and arranged to filter air and particles from a dialysate solution as it flows toward a patient and to allow substantially free, unfiltered flow of the dialysate solution away from a patient; and
- one single-compartment peritoneal dialysate container in fluid communication with said transfer tube at an opposite end of said transfer tube relative to said patient end for containment of the dialysate prior to flow toward and after flow from the patient.

19. Apparatus for the micro-evacuation of fluids from a body, comprising:
- a conduit, having a first end adapted to receive fluid from a body and a second end adapted to discharge said fluid into a disposal site;
- a pump mechanism with a chamber communicating with said conduit between said first and second ends, said pump mechanism being constructed and arranged alternately to draw fluid into said chamber from said conduit during an intake phase and to discharge fluid from said chamber into said conduit during an exhaust phase;
- a first valve operable selectively to open or close flow between said chamber and the portion of said conduit between said chamber and said first end;
- a second valve operable selectively to open or close flow between said chamber and the portion of said conduit between said chamber and said second end; and
- control means for coordinating the operation of said first and second valves with said intake and exhaust phases, whereby to alternate the direction of flow within said conduit such that there is a net flow from said first end to said second end.

* * * * *

UNITED STATES PATENT AND TRADEMARK OFFICE
CERTIFICATE OF CORRECTION

PATENT NO. : 6,129,699
DATED : October 10, 2000
INVENTOR(S) : Haight et al.

It is certified that error appears in the above-identified patent and that said Letters Patent is hereby corrected as shown below:

Title page, Item [54] and Column 1, line 1,
Title, change "PERSISTALTIC" to -- PERISTALTIC --

Title page,
Item [60], Related U.S. Application Data, change "Nov. 1, 1997" to -- Nov. 1, 1996 --.

Column 2,
Line 41, change "bidirectional" to -- bi-directional --

Column 3,
Line 3, change "Ahijopalo" to -- Ahjopalo --

Column 11,
Line 35, change "fall" to -- full --

Column 14,
Lines 15 and 18, change "+5 VDC" to -- +5VDC --
Line 19, change "+3 VDC" to -- +3VDC --

Signed and Sealed this

Fifteenth Day of June, 2004

JON W. DUDAS
*Acting Director of the United States Patent and Trademark Office*